US011656446B2

(12) United States Patent
D'Costa et al.

(10) Patent No.: US 11,656,446 B2
(45) Date of Patent: May 23, 2023

(54) DIGITAL PATHOLOGY SCANNING INTERFACE AND WORKFLOW

(71) Applicant: VENTANA MEDICAL SYSTEMS, INC., Tucson, AZ (US)

(72) Inventors: Maya D'Costa, Tucson, AZ (US); Daniela Pretorius, London (GB); Pedro De Sousa Couto E Santos, London (GB)

(73) Assignee: VENTANA MEDICAL SYSTEMS, INC., Tucson, AZ (US)

(*) Notice: Subject to any disclaimer, the term of this patent is extended or adjusted under 35 U.S.C. 154(b) by 43 days.

(21) Appl. No.: 17/010,053

(22) Filed: Sep. 2, 2020

(65) Prior Publication Data

US 2020/0400930 A1 Dec. 24, 2020

Related U.S. Application Data

(63) Continuation of application No. PCT/EP2019/055238, filed on Mar. 4, 2019.
(Continued)

(51) Int. Cl.
*G02B 21/00* (2006.01)
*G16H 10/40* (2018.01)
(Continued)

(52) U.S. Cl.
CPC ....... *G02B 21/0036* (2013.01); *G02B 21/006* (2013.01); *G16H 10/40* (2018.01);
(Continued)

(58) Field of Classification Search
CPC .. G02B 21/0036; G02B 21/006; G02B 21/34; G16H 10/40; G16H 30/20; G16H 30/40; G16H 40/67; G16H 30/00
See application file for complete search history.

(56) References Cited

U.S. PATENT DOCUMENTS

2010/0070306 A1 3/2010 Dvorak et al.
2012/0044342 A1* 2/2012 Hing .................... G02B 21/365
348/79
(Continued)

FOREIGN PATENT DOCUMENTS

JP 2007501959 A 2/2007
JP 2007233094 A 9/2007
(Continued)

OTHER PUBLICATIONS

Japan Application No. JP2020-547002 receive an Office Action, dated Nov. 26, 2021, 14 pages (8 pages English Translation, 6 pages Original Office Action).
(Continued)

*Primary Examiner* — Alazar Tilahun
(74) *Attorney, Agent, or Firm* — Kilpatrick Townsend & Stockton LLP

(57) ABSTRACT

Disclosed herein is a method of acquiring a high-resolution scan of a biological sample disposed on a substrate with a scanning device, the method comprising: receiving, on a graphical user interface, a first user input corresponding to
(Continued)

user configurable scanning settings; receiving, on a graphical user interface, a second user input to initiate scanning based on the received series of user inputs corresponding to user configurable scanning settings; and displaying, on the graphical user interface, a visualization of one or more placeholders populated with one or more of scanning operation status information, image data, and at least a portion of the user configurable scanning settings.

40 Claims, 18 Drawing Sheets

Related U.S. Application Data

(60) Provisional application No. 62/639,375, filed on Mar. 6, 2018.

(51) Int. Cl.
- *G16H 30/20* (2018.01)
- *G16H 40/67* (2018.01)
- *G16H 30/40* (2018.01)
- *G02B 21/34* (2006.01)

(52) U.S. Cl.
CPC ............ *G16H 30/20* (2018.01); *G16H 30/40* (2018.01); *G16H 40/67* (2018.01); *G02B 21/34* (2013.01)

(56) References Cited

U.S. PATENT DOCUMENTS

| | | | |
|---|---|---|---|
| 2012/0072452 A1 | 3/2012 | Stratman et al. | |
| 2014/0333959 A1* | 11/2014 | Casas | G06V 20/693 |
| | | | 358/1.15 |
| 2016/0041733 A1* | 2/2016 | Qian | G16H 30/20 |
| | | | 715/771 |
| 2016/0139387 A1* | 5/2016 | Virk | G02B 21/34 |
| | | | 348/79 |

FOREIGN PATENT DOCUMENTS

| | | |
|---|---|---|
| JP | 2012177805 A | 9/2012 |
| JP | 2013200639 A | 10/2013 |
| JP | 2014006321 A | 1/2014 |
| JP | 2014504849 A | 2/2014 |
| JP | 2014228755 A | 12/2014 |
| WO | 2013013117 | 1/2013 |
| WO | 2014089499 | 6/2014 |
| WO | 2014205557 | 12/2014 |
| WO | 2017097950 A1 | 6/2017 |

OTHER PUBLICATIONS

Application No. JP2020-547002, Office Action dated Jun. 22, 2022, 10 pages. (pp. 1-5 English translation, pp. 6-10 original document).
Application No. PCT/EP2019/055238 , International Search Report and Written Opinion, dated Aug. 12, 2019, 19 pages.
PCT/EP2019/055238 , "Invitation to Pay Additional Fees and, Where Applicable, Protest Fee", Jun. 18, 2019, 17 pages.

* cited by examiner

FIG. 5D

DIGITAL PATHOLOGY SCANNING INTERFACE AND WORKFLOW

CROSS REFERENCE TO RELATED APPLICATIONS

The present application is a continuation of International Application PCT/EP2019/055238, entitled "Digital Pathology Scanning Interface And Workflow" and filed Mar. 4, 2019, which claims priority to U.S. Provisional Patent Application No. 62/639,375, filed on Mar. 6, 2018. Each of these applications is hereby incorporated by reference herein in its entirety for all purposes.

BACKGROUND

Histopathology refers to the microscopic examination of various forms of biological samples. Specifically, in clinical medicine, histopathology refers to the examination of a biopsy or surgical sample by a pathologist, after the sample has been processed and histological sections have been placed onto glass specimen slides. Cytopathology is a branch of pathology that studies and diagnoses diseases on the cellular level. It is usually used to aid in the diagnosis of cancer, but also helps in the diagnosis of certain infectious diseases and other inflammatory conditions as well as thyroid lesions, diseases involving sterile body cavities (peritoneal, pleural, and cerebrospinal), and a wide range of other body sites. Cytopathology is generally used on samples of free cells or tissue fragments (in contrast to histopathology, which studies whole tissues).

In the past, either a lab technician or a pathologist has typically performed examination of biological samples manually. In the manual method, a slide prepared with a biological sample is viewed at a low magnification under a microscope to visually locate candidate cells of interest. Those areas of the slide where cells of interest are located are then viewed at a higher magnification to confirm those objects as cells of interest, such as tumor or cancer cells. Such a process is not only cumbersome, but time consuming. This manual process has improved with the use of digital images, i.e. photographed or scanned images of slides containing stained biological samples that have been digitized. High-resolution digital images of a biological sample are typically obtained using a microscope and specialized imaging hardware.

It is believed that access to digital specimen images has profoundly affected the field of pathology. Using digital image data relieves the technologist or pathologist from certain tasks associated with physical handling of glass specimen slides and manual manipulation of optical instruments. In addition, the use of digital images allows for automated processes for handling and manipulating images. Many organizations are attracted to digital pathology systems as a method to increase productivity and efficiency, ultimately leading to improved treatment decisions and patient care.

Digital pathology involves scanning of whole histopathology or cytopathology glass slides into digital images interpretable on a computer screen. These images are later processed by an imaging algorithm or interpreted by a pathologist. To examine biological samples, tissue sections are prepared using colored histochemical stains that bind selectively to cellular components. Color-enhanced, or stained, cellular structures are used by pathologists or a computer-aided diagnosis algorithm to identify morphological markers of a disease, and to proceed with therapy accordingly. Observing the assay enables a variety of processes, including diagnosis of disease, assessment of response to treatment, and development of new drugs to fight disease.

BRIEF SUMMARY

In one aspect of the present disclosure is a method of acquiring high-resolution images (such as those having a resolution suitable for review and analysis by a pathologist) of a biological sample with a slide scanning device, the method comprising: (i) displaying a plurality of non-overlapping placeholders, each placeholder corresponding to a slide position of a slide tray inserted in the slide scanning device, wherein each placeholder has a first portion adapted to convey image data, and a second portion adapted to convey one or more data fields; (ii) populating the second portion of each of the plurality of placeholders with at least scanning operation status information; (iii) populating the first portion of at least one of the plurality of placeholders with a preview scan image of the biological sample located at the corresponding slide position of the slide tray; and (iv) generating at least one high resolution scanned image based on received input signals corresponding to one or more selected user interface elements. In some embodiments, the preview scan image is a thumbnail image. In some embodiments, the preview scan image is a high-resolution scanned image.

In some embodiments, at least one high resolution scanned image is generated based on received input signals corresponding to one or more selected user configurable scanning settings. In some embodiments, the one or more selected user interface elements correspond to the one or more selected user configurable scanning settings. In some embodiments, the one or more selected user configurable scanning settings comprise (i) adjustments to a pre-computed area of interest; and (ii) configurable scanning parameters. In some embodiments, the adjustments to a pre-computed area of interest include at least one of resizing an area of interest, repositioning an area of interest, repositioning a focus point, creating a new area of interest, and deleting an area of interest. In some embodiments, the configurable scanning parameters include at least one of a focus method, an area of interest detection method ("AOI detection method"), a magnification, a number of focus layers, and a spacing of focus layers. In some embodiments, the configurable scanning parameters further comprise a label anonymization.

In some embodiments, both scanning operation status information and initial scanning parameters are displayed in the second portion of the plurality of placeholders (i.e. the scanning parameters used to acquire the preview scan image). In some embodiments, the scanning operation status information populated in the second portion of the placeholder is an empty status field when no slide is present in the corresponding position in the slide tray. In some embodiments, the preview scan image populated into the first portion of the at least one of the plurality of placeholders is automatically generated, and wherein the automatically generated preview scan image is acquired using pre-programmed scanning settings. In some embodiments, the pre-programmed scanning settings include at least one of a focus method and an area of interest detection method.

In some embodiments, the scanning operation status information includes at least one of alphanumeric indications, animations, and/or colored indicia. In some embodiments, the colored indicia displayed for any individual placeholder of the plurality of placeholders substantially matches a color of the corresponding individual status indicator light. In some embodiments, the slide scanner device includes an exterior panel having a plurality of status indicator lights, each status indicator light corresponding to one of the plurality of placeholders. In some embodiments, the method further comprises automatically recognizing slide label information and populating the recognized slide label information into one or more metadata fields. In some embodiments, the one or more metadata fields are DICOM attributes.

In some embodiments, the method further comprises evaluating whether the preview scan image within the at least one of the plurality of placeholders meets predetermined criteria. In some embodiments, the evaluation of the preview scan image comprises reviewing at least one magnified portion of the preview scan image for focus quality and/or image contrast. In some embodiments, the method further comprises displaying a superimposed window including a rendering of a magnified portion of the preview scan image populated into the first portion of the at least one of the plurality of placeholders. In some embodiments, the rendering of the magnified portion of the preview scan image corresponds to an image area selected with an input device.

In some embodiments, the method further comprises superimposing an area of interest over the preview scan image populated into the first portion of the at least one of the plurality of placeholders. In some embodiments, each of the plurality of placeholders are sequentially populated with preview scan images of the biological sample at the corresponding slide positions of the slide tray, and wherein the scanning operation status information is updated in real-time or substantially in real-time. In some embodiments, the method further comprises receiving a slide tray insertion signal, the slide tray insertion signal including an indication of a number of slide positions within the slide tray, and wherein a number of the plurality of non-overlapping placeholders to be displayed is determined based on the indicated number of slide positions.

In another aspect of the present disclosure is a system for generating high-resolution image scans, the system comprising: (i) one or more processors, and (ii) one or more memories coupled to the one or more processors, the one or more memories to store computer-executable instructions that, when executed by the one or more processors, cause the system to perform operations comprising: displaying a representation of a slide tray having a plurality of slide positions, wherein the representation includes a plurality of placeholders, each placeholder corresponding to one of the plurality of slide positions; populating each of the plurality of placeholders with scanning operation status information received from a scanning device; sequentially populating each of the placeholders with scanned images of biological samples received from the scanning device; and transmitting signals to the scanning device to effectuate scanning of one or more microscope slides located at one or more slide positions of the slide tray based on one or more selected user configurable scanning settings. In some embodiments, the scanned images of the biological samples are thumbnail images. In some embodiments, the scanned images of the biological samples are high-resolution images.

In some embodiments, the system further comprises instructions for displaying a magnified portion of at least one of the scanned images. In some embodiments, the magnified portion is displayed in a superimposed viewer window. In some embodiments, the one or more selected user configurable scanning settings comprise (i) adjustments to a pre-computed area of interest; and (ii) configurable scanning parameters. In some embodiments, the adjustments to a pre-computed area of interest include at least one of resizing an area of interest, repositioning an area of interest, repositioning a focus point, creating a new area of interest, and/or deleting an area of interest. In some embodiments, the configurable scanning parameters include at least a focus method, an AOI detection method, a magnification, a number of focus layers, and/or a spacing of focus layers. In some embodiments, the scanning operation status information includes at least one of alphanumeric indications, animations, and/or colored indicia. In some embodiments, the scanning device includes an exterior panel having a plurality of status indicator lights, each status indicator light corresponding to one of the plurality of placeholders. In some embodiments, the colored indicia displayed for any individual placeholder of the plurality of placeholders substantially matches a color of the corresponding individual status indicator light. In some embodiments, the system further comprises instructions for automatically recognizing slide label information within the scanned images and populating the slide label information into one or more metadata fields. In some embodiments, the one or more metadata fields are DICOM attributes.

In another aspect of the present disclosure is a non-transitory computer-readable medium storing instructions for generating high-resolution image scans with a slide scanning device, comprising: displaying a plurality of non-overlapping placeholders, each placeholder corresponding to a slide position of a slide tray inserted in the slide scanning device, wherein each placeholder has a first portion adapted to convey image data, and a second portion adapted to convey one or more data fields; populating the second portion of each of the plurality of placeholders with at least scanning operation status information; and populating the first portion of at least one of the plurality of placeholders with a preview scan image of the biological sample located at the corresponding slide position of the slide tray.

In some embodiments, the non-transitory computer-readable medium further comprises instructions for generating at least one high resolution scanned image based on received input signals corresponding to one or more selected user configurable scanning settings. In some embodiments, instructions are provided to automatically initiate a scanning operation upon insertion of the slide tray into the slide scanning device. In some embodiments, the automatically initiated scanning operation utilizes preset scanning settings. In some embodiments, the preset scanning settings include at least one of a focus method and an area of interest detection method.

In another aspect of the present disclosure is a method of acquiring a high-resolution scan of a biological sample disposed on a substrate with a scanning device, the method comprising: receiving, on a graphical user interface, a first user input corresponding to user configurable scanning settings; receiving, on a graphical user interface, a second user input to initiate scanning based on the received series of user inputs corresponding to the user configurable scanning settings; and displaying, on the graphical user interface, at least a visualization of one or more placeholders populated with one or more of (i) scanning operation status information, (ii) image data, and/or (iii) at least a portion of the user configurable scanning settings. In some embodiments, the method further comprises receiving a third user input to store the image data. In some embodiments, the storing of the image data further comprises generating a high-resolution scan of the image data prior to storage. In some embodiments, the method further comprises receiving a fourth user input to rescan image data based on a revised series of user inputs corresponding to user configurable scanning settings.

Applicant has developed a system which facilitates efficient and accurate scanning of specimen bearing slides. The system includes a novel user interface which allows a user to select or modify configurable scanning settings (e.g. user configurable scanning parameters and/or pre-computed areas of interest) after viewing one or more preview scan images (i.e. initial scanned images which may be of any resolution including, but not limited to, thumbnail images, low-resolution images, or high-resolution images), scanning operation status information, and/or already applied scanning settings. Accordingly, the system and accompanying method allows a user to dynamically vary user configurable scanning settings while being provided real-time image data, scanning operation status data, and scanning setting information such that a final scan may be acquired that meets certain criteria or objectives (e.g. pathologist preferences, assay or protocol requirements, etc.). Applicants submit that the system and methods disclosed herein facilitate increased scanning speeds and increased efficiencies in the acquisition of image data. Applicants further submit that the system and methods disclosed herein enable increased accuracy in the scanning of microscope slides.

BRIEF DESCRIPTION OF THE DRAWINGS

For a general understanding of the features of the disclosure, reference is made to the drawings. In the drawings, like reference numerals have been used throughout to identify identical elements.

FIG. 5D illustrates a user interface setting forth a representation of a slide tray having six slide positions, the representation including six placeholders, where all six placeholders indicate that image scans (e.g. high-resolution image scans or thumbnail image scans) are complete, along with a visualization of the acquired image data and scanning settings utilized. Also illustrated are the label portions of each scanned slide, the label portions including slide label information such as barcodes and/or alphanumeric information, in accordance with some embodiments.

DETAILED DESCRIPTION

Figure 1A:
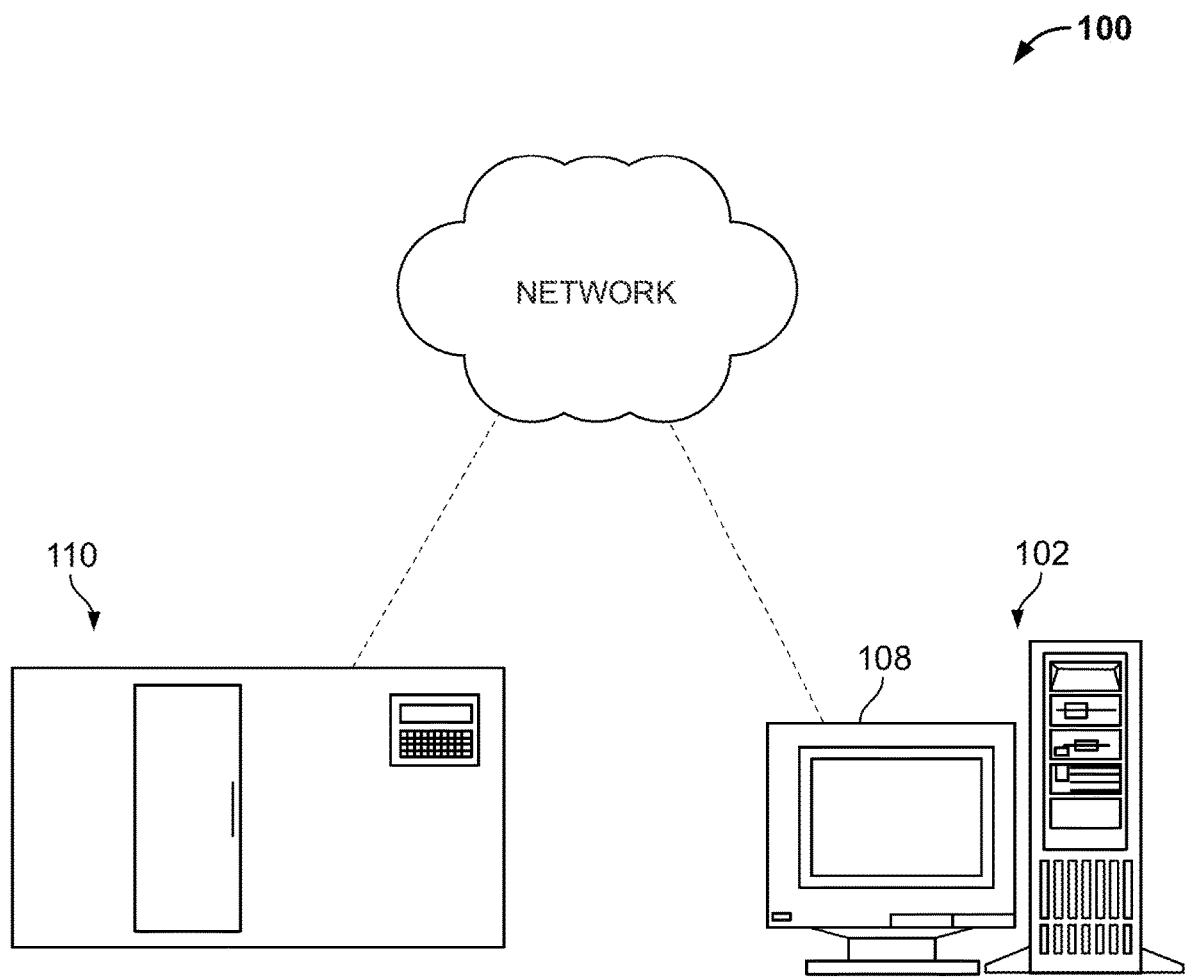
FIG. 1A illustrates a scanning system including a computer having one or more processors and a scanning device, where the computer and the scanning device are communicatively coupled, such as through a network, in accordance with some embodiments.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of" when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the phrase "area of interest" means a region of a slide that may be automatically or manually selected for scanning, or that has been scanned.

As used herein, the term "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the terms "image data", "scanned image data" or the like encompass raw image data acquired from the biological tissue sample, such as by means of an optical sensor or sensor array, or pre-processed image data. In particular, the image data may comprise a pixel matrix.

As used herein, the terms "image," "image scan," or "scanned image" encompass raw image data acquired from the biological tissue sample, such as by means of an optical sensor or sensor array, or pre-processed image data.

As used herein, the term "slide" refers to any substrate (e.g., substrates made, in whole or in part, glass, quartz, plastic, silicon, etc.) of any suitable dimensions on which a biological sample is placed for analysis, and more particularly to a "microscope slide" such as a standard 3 inch by 1 inch microscope slide or a standard 75 mm by 25 mm microscope slide. Examples of biological samples that can be placed on a slide include, without limitation, a cytological smear, a thin tissue section (such as from a biopsy), and an array of biological samples, for example a tissue array, a cellular array, a DNA array, an RNA array, a protein array, or any combination thereof. Thus, in one embodiment, tissue sections, DNA samples, RNA samples, and/or proteins are placed on a slide at particular locations. In some embodiments, the term slide may refer to SELDI and MALDI chips, and silicon wafers.

As used herein, the terms "stain," "staining," or the like as used herein generally refers to any treatment of a biological sample that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological sample. For example, staining can provide contrast between a particular molecule or a particular cellular structure and surrounding portions of a biological sample, and the intensity of the staining can provide a measure of the amount of a particular molecule in the sample. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the term "user interface" refers to a program enabling a user, for example histologists, cytologists, pathologists, etc., to input commands and data and receive results. In some embodiments, the user interface is a graphical user interface (GUI). The terms "user interface" and "graphical user interface" are used interchangeably herein.

As described in further detail herein, the present disclosure facilitates the acquisition and/or the processing of image data, such as from a scan of a biological sample disposed on a substrate, according to the needs or preferences of a user (e.g. a technician, a histologist, a cytologist, a pathologist, etc.) or the requirements established for a particular assay or scoring methodology. The disclosed user interface and methods of interacting with the user interface are believed to enable an efficient workflow by users of the system.

FIG. 1A sets forth a scanning system 100 (e.g. a scanning system for digital pathology) including a scanning device 110 communicatively coupled to a processing subsystem 102. The scanning device 110 can be coupled to the processing subsystem 102 either directly (e.g., through one or more communication cables) or through one or more wired and/or wireless networks. In some embodiments, the processing subsystem 102 may be included in or integrated with the scanning device 110. The processing subsystem 102 may include a display 108 and one or more input devices (not illustrated) for receiving commands from a user. In some embodiments, either the processing subsystem 102 or the scanning device 110 may be coupled to a network, where the network may include or be coupled to a storage system where image data and/or patient information may be stored for later viewing and/or analysis. In some embodiments, a user interface is rendered by processing subsystem 102 and is provided on display 108 to facilitate the acquisition of image data from scanning device 110, and subsequent evaluation of the image data, where elements of the user interface may provide feedback to a user as to the status of any scanning operation being performed by the scanning device 110. The user interface may also provide for the selection of user configurable scanning settings such that a scanning operation may be commanded according to user inputs.

Figure 1B:
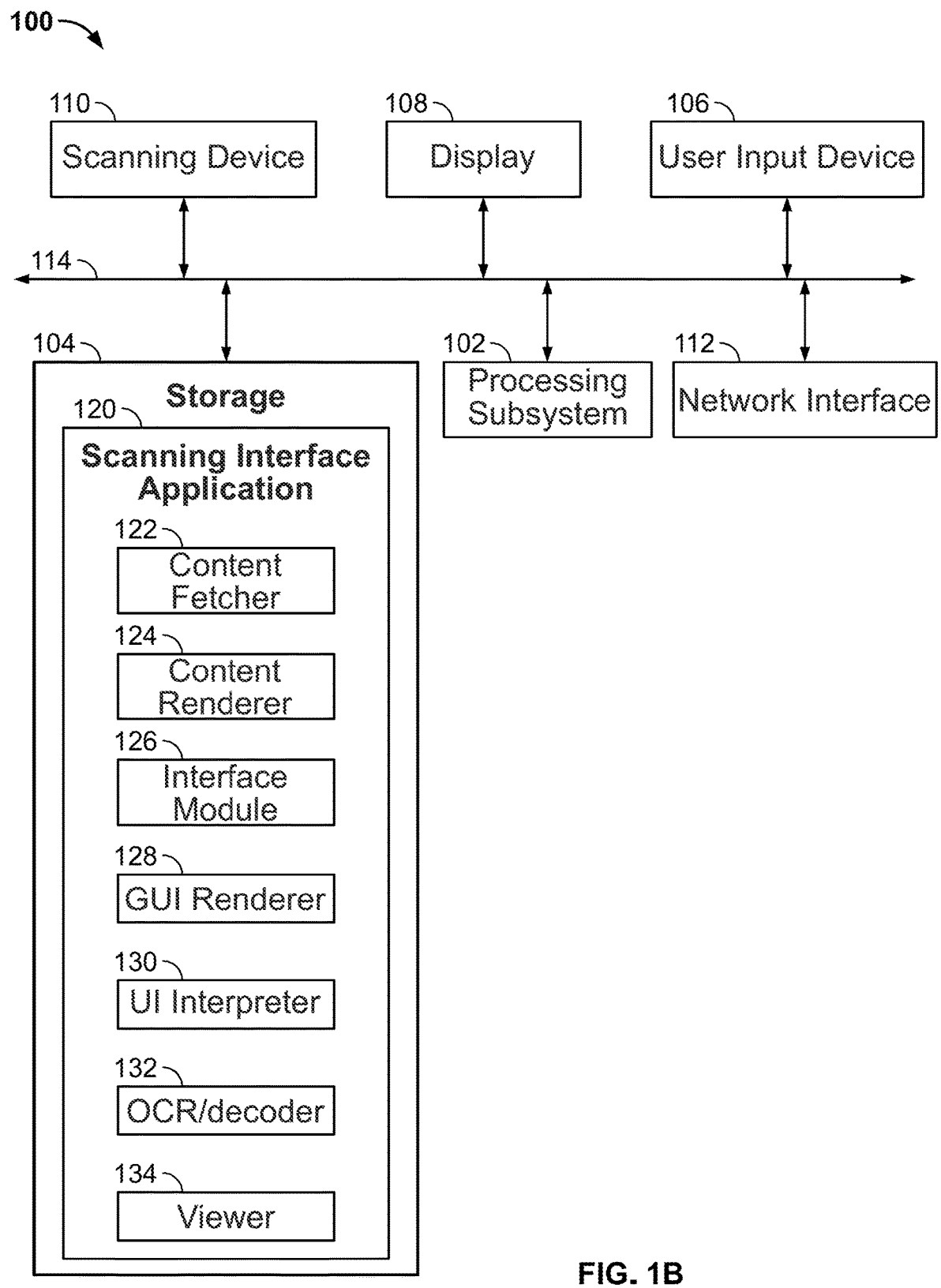
FIG. 1B illustrates a scanning system including a processing subsystem, a scanning device, a storage subsystem, an output device, and an input device, each of the components communicatively coupled through a bus, a network, or other wired or wireless interconnect, in accordance with some embodiments.

FIG. 1B is a block diagram of a scanning system 100 according to an embodiment of the present disclosure. Scanning system 100 can be implemented using any type of user-operable computing device, including desktop computers, laptop computers, tablet computers, handheld devices (e.g., smart phones, media players), and so on. The scanning system 100 can include a number of interconnected components such as processing subsystem 102, storage subsystem 104, input device 106, display 108, scanning device 110 and network interface 112 communicating via bus 114, as discussed in more detail below.

Processing subsystem 102 can include a single processor, which can have one or more cores, or multiple processors, each having one or more cores. In some embodiments, processing subsystem 102 can include one or more general-purpose processors (e.g., CPUs), special-purpose processors such as graphics processors (GPUs), digital signal processors, or any combination of these and other types of processors. In some embodiments, some or all processors in processing subsystem can be implemented using customized circuits, such as application specific integrated circuits (ASICs) or field programmable gate arrays (FPGAs). In some embodiments, such integrated circuits execute instructions that are stored on the circuit itself. In other embodiments, processing subsystem 102 can retrieve and execute instructions stored in storage subsystem 104. For example, processing subsystem can execute instructions to receive and process image data from the scanning device 110, to display a user interface having selectable scanning settings, etc.

Storage subsystem 104 can include various memory units such as a system memory, a read-only memory (ROM), and a permanent storage device. A ROM can store static data and instructions that are needed by processing subsystem 102 and other modules of scanning system 100. The permanent storage device can be a read-and-write memory device. This permanent storage device can be a non-volatile memory unit that stores instructions and data even when scanning system 100 is powered down. In some embodiments, a mass-storage device (such as a magnetic or optical disk or flash memory) can be used as a permanent storage device. Other embodiments can use a removable storage device (e.g., a flash drive) as a permanent storage device. The system memory can be a read-and-write memory device or a volatile read-and-write memory, such as dynamic random access memory. The system memory can store some or all of the instructions and data that the processor needs at runtime.

Storage subsystem 104 can include any combination of non-transitory computer readable storage media including semiconductor memory chips of various types (DRAM, SRAM, SDRAM, flash memory, programmable read-only memory) and so on. Magnetic and/or optical disks can also be used. In some embodiments, storage subsystem 104 can include removable storage media that can be readable and/or writeable; examples of such media include compact disc (CD), read-only digital versatile disc (e.g., DVD-ROM, dual-layer DVD-ROM), read-only and recordable Blu-ray® disks, ultra-density optical disks, flash memory cards (e.g., SD cards, mini-SD cards, micro-SD cards, etc.), and so on. In some embodiments, data and other information can be stored in one or more remote locations, e.g., cloud storage, and synchronized with other the components of the scanning system 100.

In some embodiments, storage subsystem 104 can store one or more software programs to be executed by processing subsystem 102, such as a scanning interface application 120 or an image viewer application. "Software" refers generally to sequences of instructions that, when executed by processing subsystem 102, cause scanning system 100 to perform various operations, thus defining one or more specific machine implementations that execute and perform the operations of the software programs. Thus, "software" can also include firmware or embedded applications or any other type of instructions readable and executable by processing subsystem 102. Software can be implemented as a single program or a collection of separate programs or program modules that interact as desired. In some embodiments, programs and/or data can be stored in non-volatile storage and copied in whole or in part to volatile working memory during program execution. From storage subsystem 104, processing subsystem 102 can retrieve program instructions to execute and data to process in order to execute various operations including operations described below. Examples of software include, but are not limited to, scanning interface software (e.g. to select settings for scanning and to enable the acquisition of scanned image data) and image viewer software (e.g. to view and/or analyze scanned image data).

A user interface can be provided to a display device 108, and/or and one or more other user output devices (not shown). Input devices 106 can include any device via which a user can provide signals to scanning system 100; scanning system 100 can interpret the signals as indicative of particular user requests or information. For example, and as disclosed further herein, the user may select certain user configurable scanning settings displayed within the user interface, whereby signals generated by the selection may cause the scanning device 110 to capture image data based on the selected configuration settings. In various embodiments, input devices 106 can include any or all of a keyboard, touch pad, touch screen (e.g., a touch-sensitive overlay on a display surface of display 108), mouse or other pointing device, scroll wheel, click wheel, dial, button, switch, keypad, microphone, and so on.

Display 108 can display images generated by scanning system 100 and can include various image generation technologies, e.g., a cathode ray tube (CRT), liquid crystal display (LCD), light-emitting diode (LED) including organic light-emitting diodes (OLED), projection system, or the like, together with supporting electronics (e.g., digital-to-analog or analog-to-digital converters, signal processors, or the like). Some embodiments can include a device such as a touchscreen that function as both input and output device. In some embodiments, other user output devices can be provided in addition to or instead of display 108. Examples include indicator lights present on scanning device 110, speakers, tactile "display" devices, printers, and so on.

In some embodiments, the scanning device 110 may include a plurality of indicator lights or status lights, the indicator or status lights capable of displaying a plurality of colors, such as first, second, third, and fourth colors, or no color (i.e. the status indicator may remain clear or unilluminated). In some embodiments, scanning device 110 simultaneously provides signals to the indicator lights or status lights and to processing subsystem 102 such that the status of a scanning operation may be contemporaneously visualized by indicia on the scanning device 110 itself and/or within a user interface, as provided herein. In this way, multiple sources of feedback can be provided to the user of the scanning system 100. In some embodiments, the multiple sources of feedback are substantially synchronized with one another, enabling an immersive user experience.

In some embodiments, the user interface can provide a graphical user interface, in which visible image elements in certain areas of display 108 are defined as active elements or control elements that the user selects using input devices 106. For example, the user can manipulate an input device 106 to position an on-screen cursor or pointer over the control element, then "click" a button to indicate the selection (the selection sending signals to perform a designated action or routine). For example, the user can manipulate the input device 106 to select an icon within the user interface which would effectuate the initiation of a scanning operation, stop a scanning operation, eject a slide tray, launch viewer module 134 or other viewer software, initiate area of interest adjustments, etc. In some embodiments, such elements are arranged along a "menu bar" and, in some embodiments, like actions or routines are grouped together (e.g. scanning operation actions are grouped together, viewer actions are grouped together, etc.).

Likewise, the user can manipulate the input device 106 so as to interact with a series of user configurable options (icons, buttons, context menus, dropdown menus, toggle switches, etc.) so as to define a set of user configurable scanning settings which, when selected, would allow one or more scanning operations to commence using the selected scanning settings. In some embodiments, and as described further herein, the input device 106 may be utilized such that user configurable scanning settings are selected with the input device 106 so that images acquired during a scanning operation with the scanning device 110 adhere to user preferences, or the standards required for performing or analyzing a particular biological sample.

Alternatively, the user can touch the control element (e.g., with a finger or stylus) on a touchscreen device. In some embodiments, the user can speak one or more words associated with the control element (the word can be, e.g., an identifier on the element or a function associated with the element). In some embodiments, user gestures on a touch-sensitive device can be recognized and interpreted as input commands; these gestures can be, but need not be, associated with any particular area on display 108. Other user interfaces can also be implemented.

Scanning device 110 can collect image data from samples mounted on a substrate, e.g. biological samples disposed on a microscope slide. The scanning device 110 can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the sample. In some embodiments, the scanning 110 device also includes the ability to send signals to other system components, such as signals including image data, scanning operation status data, and/or slide tray insertion signals. The scanning device 110 may receive signals from the processing subsystem 102 such that scanning may be initiated or stopped according to user configurable scanning settings, and such that slide tray ejection may be performed through the selection of an element within the user interface.

In some embodiments, the scanning device 110 includes a line scan detector. In some embodiments, the scanning device 110 includes an imaging lens which focuses light originating from a sample located on a slide onto a line scan detector. As the detector is a line scan detector, the image area is an elongate region extending in a swathe width direction 5 (x-axis). In some embodiments, a swathe defines the width of tissue that can be imaged by the sensor perpendicular to the scan direction. At 20× magnification, the swathe width in standard scan mode is about 1.2 mm. At 40× magnification, the swathe width is approximately about 1 mm. Parameters of the line scanning operation may be set, in some embodiments, through user configurable scanning settings presented by the user interface.

The imaging lens and the line scan detector together make up an imaging system of the scanning device 110. In some embodiments, in order to produce an extended image over a large area of the sample located on the slide, the slide is moved (by moving the slide mounting device) relative to the imaging lens and line scan detector in a scan length direction (y-axis). In this sense the sample on the slide is "scanned" by the line scan detector. PCT Publication No. WO/2017/097950 discloses other line scan detectors and their methods of use, the disclosures of which are hereby incorporated by reference herein in their entireties.

Network interface 112 may provide data communication capability for scanning system 100. In some embodiments, network interface 112 can include radio frequency (RF) transceiver components for accessing wireless voice and/or data networks (e.g., using cellular telephone technology, advanced data network technology such as 3G, 4G or EDGE, WiFi (IEEE 802.11 family standards), or other mobile communication technologies, or any combination thereof, GPS receiver components, and/or other components. In some embodiments, network interface 112 can provide wired network connectivity (e.g., Ethernet) in addition to or instead of a wireless interface. Network interface 112 can be implemented using a combination of hardware (e.g., antennas, modulators/demodulators, encoders/decoders, and other analog and/or digital signal processing circuits) and software components.

Bus 114 can include various system, peripheral, and chipset buses that communicatively connect the numerous components of scanning system 100. For example, bus 114 can communicatively couple processing subsystem 102 with storage subsystem 104. Likewise, bus 114 can communicatively couple the scanning device (and any subsystems disposed therein) to the processing subsystem 102. Bus 114 can also connect to input devices 106 and display 108. Bus 114 can also couple processing subsystem 102 to a network through network interface 112. In this manner, scanning system 100 can be connected to a network of multiple computer systems (e.g., a local area network (LAN), a wide area network (WAN), an Intranet, or a network of networks, such as the Internet. Any or all components of scanning system 100 can be used in conjunction with the disclosure.

Some embodiments include electronic components, such as microprocessors, storage and memory that store computer program instructions in a computer readable storage medium. Many of the features described herein may be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter.

Through suitable programming, processing subsystem 102 can provide various functionalities for scanning system 100. For example, processing subsystem 102 can execute a scanning interface application 120 having a user interface; or can execute a viewer application enabling the review, analysis, and/or annotation of displayed or stored images and/or metadata. Scanning interface application 120 can provide various functionality such as the ability to retrieve and display content (e.g. image data, scanner operation status information) from scanning device 110; or command the scanning device to perform scanning operations using user configurable scanning settings, and to send the resulting image data (e.g. a preview scan, a high resolutions scan, etc.) acquired during a scanning operation to, for example, the processing subsystem 102, the storage subsystem 104, and/or to network interface 112. In addition, the scanning interface application 120 can retrieve and display content (e.g. stored image data and/or patient data) from storage subsystem 104 and also provide the ability to receive and interpret user input pertaining to the content items (e.g. selection of an image or series of images or any portion thereof for viewing, including viewing in the scanning interface application using viewer module 134 or within a separate image viewing, annotation, and analysis software application).

In some embodiments, scanning interface application 120 incorporates various interoperating modules (e.g., blocks of code) that, when executed by one or more processors within the processing subsystem 102, implement aspects of the scanning interface operation. For example, scanning interface application 120 can include a content fetcher 122, a content renderer 124, an interface module 126, a GUI renderer 128, a UI interpreter 130, an OCR/decoder module 132, and a viewer module 134.

In some embodiments, content fetcher 122 can include instructions for interacting with scanning device 110 or network interface 112 to fetch or otherwise retrieve the content items (e.g. scanned image data, status data, etc.). In some embodiments, content renderer 124 can include instructions for interpreting fetched content items and rendering displayable images, such as scanned images of biological samples. In some embodiments, content renderer 124 can also process the collected data, e.g., by applying any pre-processing to the acquired scanned images. In some embodiments, interface module 126 includes instructions to control the operation of scanning device 110 so that scanned images of one or more biological samples may be obtained according to user configurable scanning settings (e.g. focus, scan volume, area of interest, magnification, etc.).

Figure 4A:
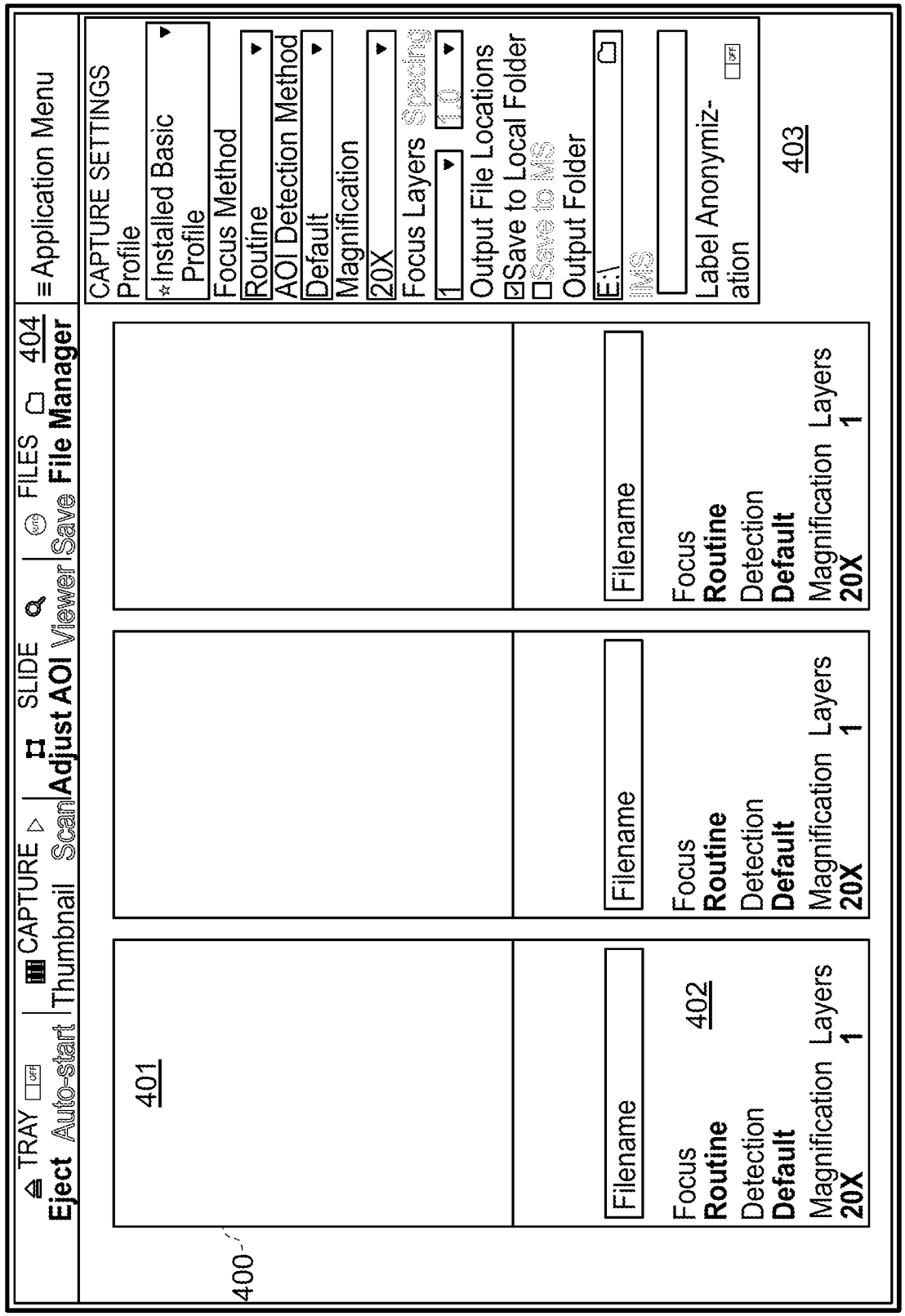
FIG. 4A illustrates a user interface including a representation having three discrete placeholders, each placeholder representing a slide position in a slide tray having a total of three slide positions, and wherein each placeholder displayed within the user interface corresponds to the corresponding slide position in the slide tray, in accordance with some embodiments.
Figure 4B:
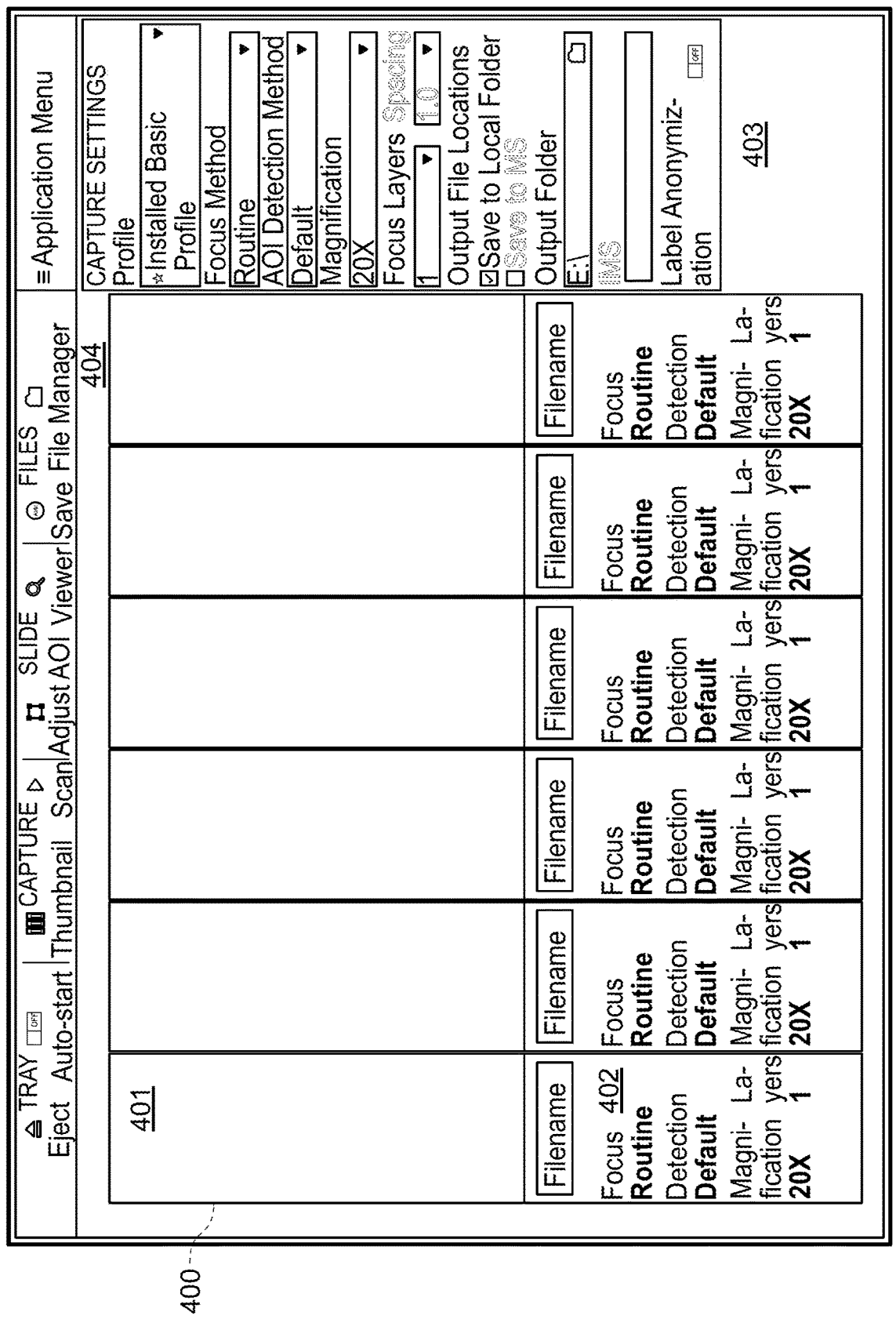
FIG. 4B illustrates a user interface including a representation having six discrete placeholders, each placeholder representing a slide position in a slide tray having a total of six slide positions, and wherein each placeholder displayed within the user interface corresponds to the corresponding slide position in the slide tray, in accordance with some embodiments.

In some embodiments, GUI renderer 128 creates graphical user interface (GUI) elements to be presented to the user along with the content items rendered by content renderer 124 or other system modules. GUI renderer 128 can include code defining the location and appearance of GUI elements, such as a menu bar, viewer window overlays, scanning parameter configuration panels, pop-up menus, etc. In some embodiments, GUI renderer 128 can incorporate scanned image data provided from the interface module 126 into some or all of the GUI elements (e.g. an actual image of a scanned biological sample may be displayed within a placeholder within the user interface, etc.). Likewise, the GUI renderer 128 can incorporate status information from the interface module 126 so as to visually provide the status of any scanning operation to the user (i.e. scanning operation status information may be populated into portions of the appropriate placeholders, such as in real-time as scanning operation status information is received from the scanning device 110). The GUI rendered 128 may also provide a workspace such that a user may interact with the scanning system 100 and/or control operations of the scanning device 110. In some embodiments, such as depicted in FIGS. 4A and 4B, the workspace includes (i) representations of slide positions in a slide tray, the slide positions each adapted to convey image data in a first placeholder portion 401 and/or convey one or more data fields in a second placeholder portion 402 (e.g. a scanning status data field), (ii) a panel allowing the selection of user configurable scanning parameters 403, and (iii) a menu bar 404.

UI interpreter 130 can receive user input, e.g., via an input device 106, and can interpret the input to determine actions to be performed by scanning interface application 120. For example, UI interpreter 130 can determine which GUI element (e.g. an icon, or a selectable item in menu, context menu, dropdown list, buttons, etc.) the user selected and initiate the corresponding action (e.g., initiating scanning or rescanning based on the selection of user configurable scanning settings or stored scanning parameter presets, launch a view window, launch a viewer program, initiate a high-resolution scan, eject a slide tray, etc.).

In some embodiments, the OCR/decoder module 132 includes instructions which enable the optical character recognition of slide label information (e.g. alphanumeric information or information included within a barcode) provided on a label portion of a substrate, e.g. a microscope slide. Likewise, the OCR/decoder module 132 includes instructions which enable information to be extracted from a barcode or other indicia including embedded information. In some embodiments, the OCR/decoder module 132 includes instructions which enable the recognized and/or decoded information to be populated into appropriate data fields. In some embodiments, at least one user configurable scanning setting may be automatically changed based on the automatically recognized slide label information. Indeed, barcode information could be used to establish any configurable scanner setting, including any of those described herein. For example, barcode info can indicate a certain type of slide (e.g., type of cancer and type of stain) and the scanning device can recognize that type of slide and set scanning settings associated with that specific type of slide. Scanning settings can include the number of layers in the Z-stack, AOI shape, AOI size, magnification, etc.

In some embodiments, the OCR/decoder module 132 enables the population of DICOM attributes. For example, the OCR/decoder module 132 allows for (i) the reading of barcode information, and/or (ii) the assignment of the decoded information into patient attribute fields (e.g. patient name, patient ID, patient date of birth, patient sex, study attributes, study ID, accession number, etc.). In other embodiments, the OCR/decoder module 132 enables the generation of file names based on barcode information or other indicia present on the label portion of the slide.

In some embodiments, the viewer module 134 allows for the viewing of a portion or region of an acquired image within the user interface, i.e. without having to switch to a separate application. In some embodiments, the viewer module 134 facilities the viewing of a region or portion of the acquired image using inputs received from an input device 106. In this way, the user may position, for example, crosshairs (or such as a mouse pointer) over an area of the image and then the viewer module 134 will display a magnified portion of the image for that particular selected area. In some embodiments, the viewer module 134 may be dynamically repositioned throughout the user interface such that it "floats" over any placeholder or other user interface element. The viewer module 134 may be resized to accommodate user preferences and/or the size of the magnified portion displayed.

It will be appreciated that scanning system 100 is illustrative and that variations and modifications are possible. Further, while scanning system 100 is described with reference to particular blocks, it is to be understood that these blocks are defined for convenience of description and are not intended to imply a particular physical arrangement of component parts. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software. Scanning interface application 120 is also illustrative, and specific implementations may include more or fewer modules than described herein. Moreover, while a particular module may be described as performing a particular function, such descriptions are not intended to imply a particular function performed by the module or a particular set of instructions included within such module.

Figure 2A:
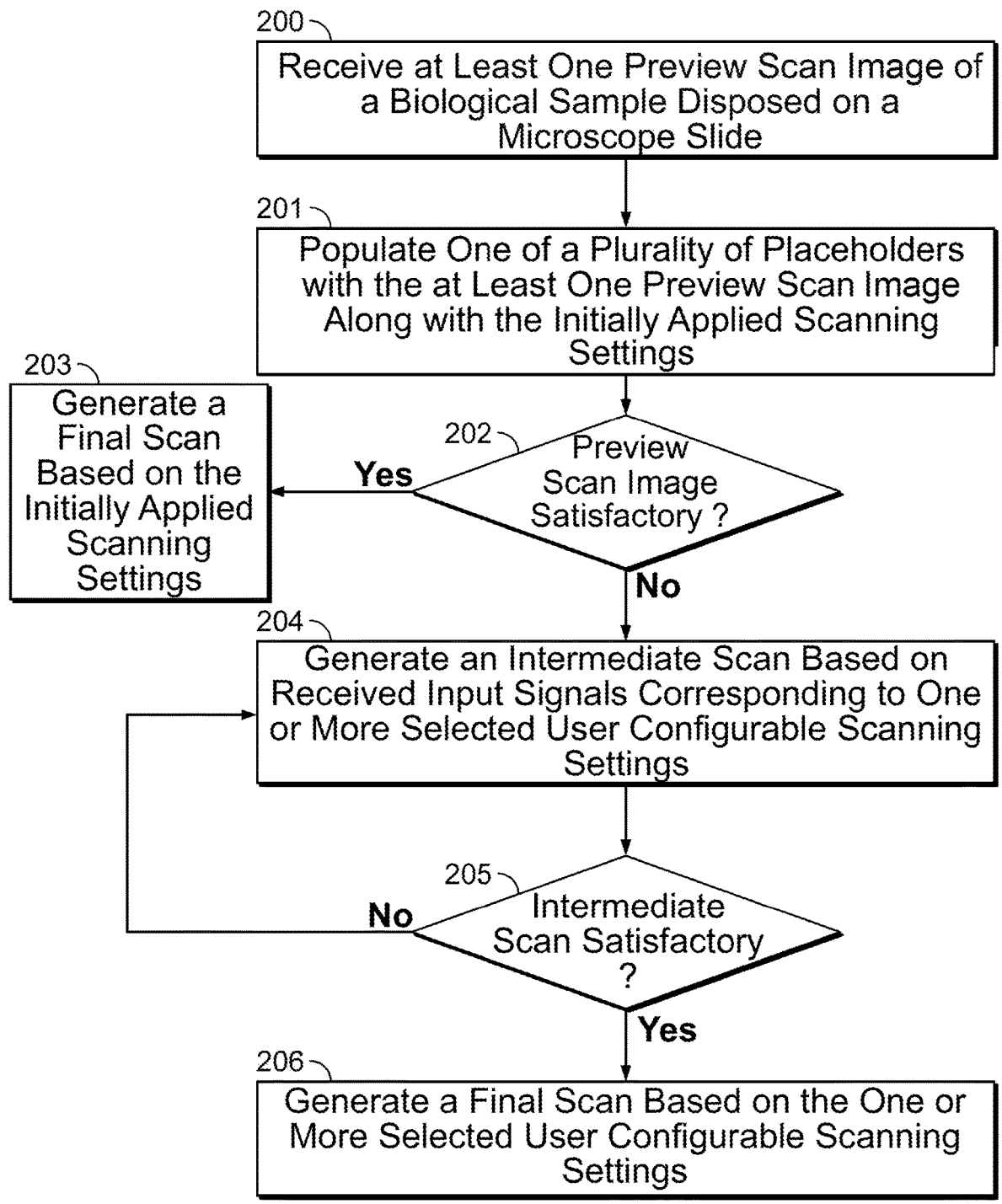
FIG. 2A sets forth a flowchart illustrating the steps of generating a high-resolution scan of a biological sample disposed on a substrate (e.g. a microscope slide) using a scanning device, in accordance with some embodiments.
Figure 2B:
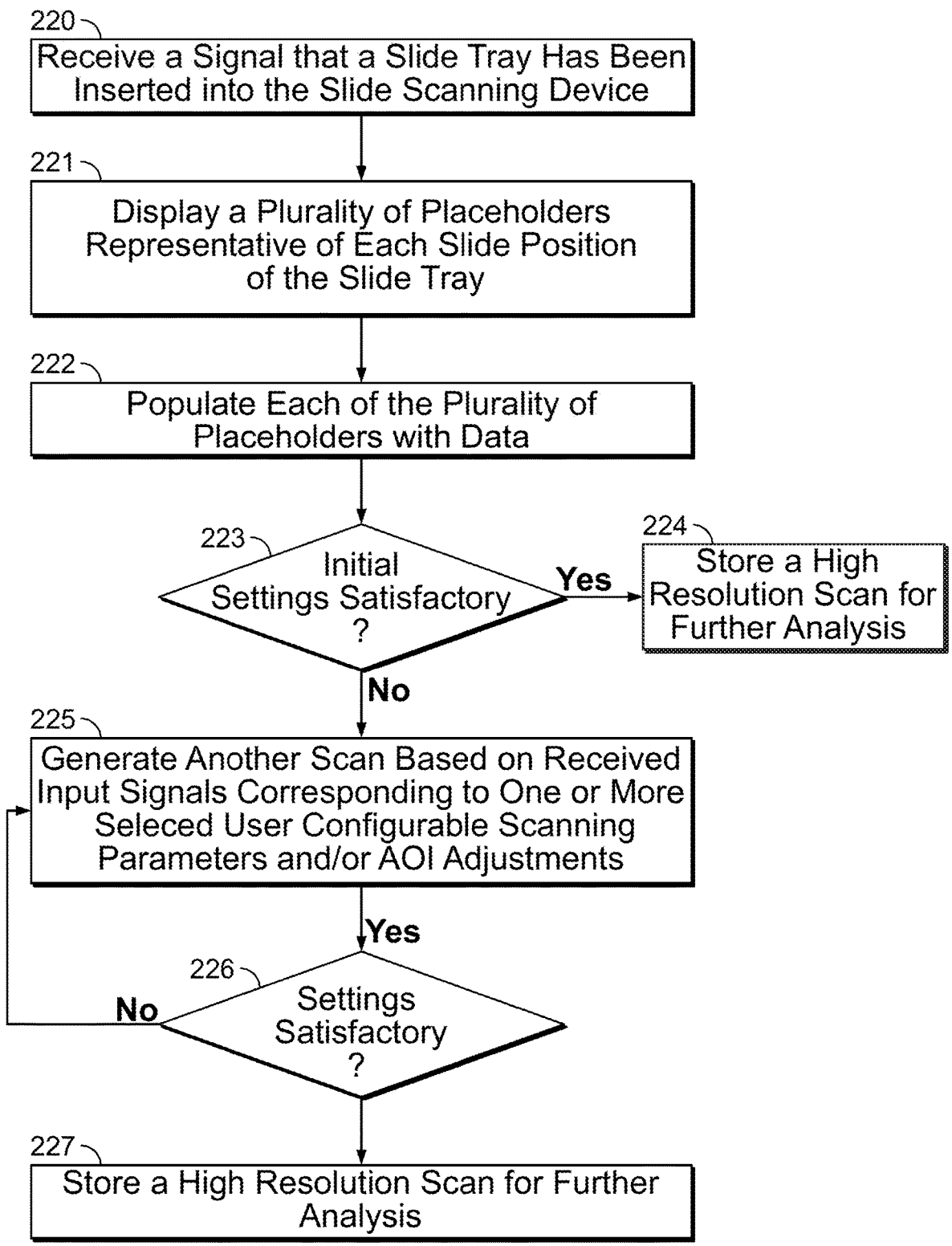
FIG. 2B sets forth a flowchart illustrating the data exchange between a scanning device and a processing subsystem, the processing subsystem providing feedback to a user and further enabling the system user to modify scanning settings such that a high-resolution scan having user configurable attributes is generated, in accordance with some embodiments.

FIGS. 2A and 2B set forth flowcharts depicting the steps involved in acquiring a scan of a biological sample disposed on a substrate, e.g. a microscope slide. In some embodiments, the scan is acquired in accordance with user configurable scanning settings which may be selected by the user (e.g. manually or according to a predetermined configuration profile). In some embodiments, the user configurable scanning settings may be optimized after a user reviews one or more preview scan images of the biological sample acquired by the scanning device 110. In some embodiments, the method is facilitated in an efficient manner through the use of a novel user interface which allows a user to select or modify configurable scanning settings (e.g. user configurable scanning parameters or pre-computed areas of interest) after viewing one or more preview scan images. In some embodiments, the selected user configurable scanning settings (and those which were applied during the scanning operation) are displayed adjacent to the one or more preview scan images to which they correspond. As described in further detail herein, the method allows a user to dynamically vary user configurable scanning settings while being provided real-time image data, scanning operation status data, and scanning setting information such that a final scan may be acquired that meets certain criteria or objectives (e.g. pathologist preferences, assay or protocol requirements, etc.).

With reference to FIG. 2A, at least one preview scan image of a biological sample disposed on a microscope slide is generated by scanning device 110 and received by scanning interface application 120 (step 200). The at least one preview scan image may be automatically acquired according to a preset enabled within the scanning interface application 120, or the preview scan image may be acquired manually (i.e. by a user selecting one or more user interface elements using input device 106 which causes a scanning operation to commence). In embodiments where the preview scan image is acquired automatically, the scanning operation may be commenced using a pre-determined set of scanning settings stored within the storage subsystem 104, e.g. a presets file.

The received at least one preview scan image is then populated into one of a plurality of placeholders displayed by the user interface (step 201). In some embodiments, the preview scan image is populated into a placeholder that corresponds to a slide position of a slide tray inserted into the scanning device 110. In this way, the placeholders displayed accurately represent the slide positions of the actual slide tray inserted into the scanning device 110. In some embodiments, such as depicted in FIGS. 4A and 4B, the placeholders are arranged in parallel relative to each other and/or relative to a capture or scanning settings panel. In some embodiments, the placeholders are displayed in a vertical arrangement. In some embodiments, an area of interest ("AOI") is superimposed over the preview scan image. The representations of the placeholders within the user interface and the various slide tray embodiments are described in further detail herein.

In some embodiments, the placeholders are also populated with the set of configurable scanning settings which were used in acquiring the respective preview scan image. In some embodiments, the identification of the set of scanning settings which were used in acquiring the respective preview scan image include one or more of (i) the focus method, (ii) the detection method, (iii) the magnification, (iv) the number of layers scanned, and/or (v) the spacing between scanned layers. In this way, the user of the scanning system 100 is presented with the preview scan image and the relevant scanning parameter information which would allow the user to make an informed determination as to whether the preview scan image is satisfactory for a given purpose (step 203). To further facilitate the review of the preview scan image, viewer module 134 may be utilized to view regions or portions of the preview scan image, such as a magnified portion of the preview scan image, according to user inputs. In addition, or as an alternative to the viewer module 134, separate viewer software (provided on storage subsystem 104) may be run by the processing subsystem 10 to review the preview scan image or any portion thereof. In some embodiments, the viewer module 134 or stand-alone viewer software may enable viewing of different focus layers so as to determine whether an appropriate focus layer spacing was selected.

If the preview scan image is satisfactory, the user may elect to have the preview scan image stored, such as in storage subsystem 104, assuming the preview scan image is of a resolution sufficient for further analysis (e.g. if the preview scan image is a high-resolution image, then that high-resolution image may be stored without further rescanning). If, on the other hand, a higher resolution scan is needed, the user may select user interface elements which, when selected, provide commands to the scanning device 110 to acquire a high-resolution scan of the biological sample using the same scanning settings used for the preview scan image. For example, the user may select a user interface element that sends a signal to the interface module 126 such that high-resolution scanning, according to the selected scanning settings, is initiated by the scanning device 110 using the previously used scanning settings. In some embodiments, a high-resolutions comprises a greater number of dots-per-inch (dpi) inch than a low-resolution image, such as a thumbnail image. In some embodiments, the dpi of a high-resolution image ranges from 150 dpi to 1200 dpi. In some embodiments, the dpi of a high-resolution image ranges from 200 dpi to 1200 dpi. In other embodiments, the dpi of a high-resolution image ranges from 300 dpi to 1200 dpi. In other embodiments, the dpi of a high-resolution image ranges from 600 dpi to 1200 dpi.

If the preview scan image is not satisfactory, user configurable scanning settings may be selected, such as by selecting from a plurality of elements (e.g. dropdown lists, toggle switches, etc.) displayed in a settings panel or a menu bar within the user interface. For example, the user interface may provide selectable user configurable scanning parameters including a choice of one or more of (i) a focus method, (ii) an AOI detection method, (iii) a magnification level, (iv) the number of focus layers to scan, and/or (v) the spacing between focus layers.

In some embodiments, the user is also afforded the ability to alter scanning settings including a pre-computed area of interest ("AOI"), again using inputs from input device 106. For example, the user may select a user interface element that enables adjusting one or more of the location, size, and/or focus point of an AOI. In some embodiments, the user inputs allow for one or more of real-time resizing of the pre-computed AOI, real-time repositioning of the pre-computed AOI bounding box, real-time deletion of one or more pre-computed AOIs, real-time AOI focus point selection, or the real-time outlining of a new AOI. In some embodiments, the AOI may be adjusted through user inputs to minimize white space surrounding the tissue, thereby decreasing, for example, a scanning time of a scanning operation of scanning device 110. Alternatively, the AOI may be adjusted through user inputs to increase the size of any pre-computed AOI bounding box such that tissue missed by an automated detection method may be captured. In some embodiments, the scanning interface application 120 and/or interface module 126, upon receipt of user input commands, may direct the scanning device 110 to acquire a scan using the set of selected user configurable scanning settings with or without changes made to any pre-computed AOI (step 204).

At step 205, the user may again make a determination as to whether the intermediate scan generated is satisfactory (i.e. meets predetermined scanning criteria) and, if so, may store the intermediate scan or generate a higher resolution version of the intermediate scan (using the same set of scanning settings) for storage (step 206). Of course, if the intermediate scan is not satisfactory, the sample may be rescanned with yet a further different set of user configurable scanning settings (such as a set of scanning settings where at least one setting is changed). This process may be repeated (e.g. acquiring second, third, fourth, etc. image scans) until a satisfactory scan is acquired, i.e. one that meets pre-determined criteria or objectives, including pathologist preferences, assay or protocol requirements, etc.

In some embodiments, the user interface provides elements which enable the selection of a specific file format for saving, including the DICOM format. In some embodiments, the user interface enables the manual entry of metadata before, during, or after the file save operation. In other embodiments, metadata is automatically recognized and imported using OCR/decoder module 132 into appropriate data fields or within the filename itself. In some embodiments, the user interface may display a separate window which includes metadata fields for population and/or viewing, and whereby the metadata may be stored along with any imaging data.

FIG. 2B sets forth a flowchart illustrating the steps of acquiring a scanned image of a biological sample disposed on a substrate using slide scanning device 110. Step 220 involves receiving from the slide scanning device 110 a slide tray insertion signal which is indicative of a slide tray being inserted into the slide scanning device 110. The slide tray may include one or more slides having biological samples disposed thereon, e.g. one slide, two slides, three slides, four, slides, five slides, six slides, etc. In some embodiments, the slide tray insertion signal received from the slide scanning device 110 includes an indication of the type of slide tray inserted, e.g. whether a slide tray having 3 or 6 slide positions is inserted (as described below). In some embodiments, the slide tray insertion signal may also indicate whether a particular slide position in the slide tray is occupied with a microscope slide.

Figure 3A:
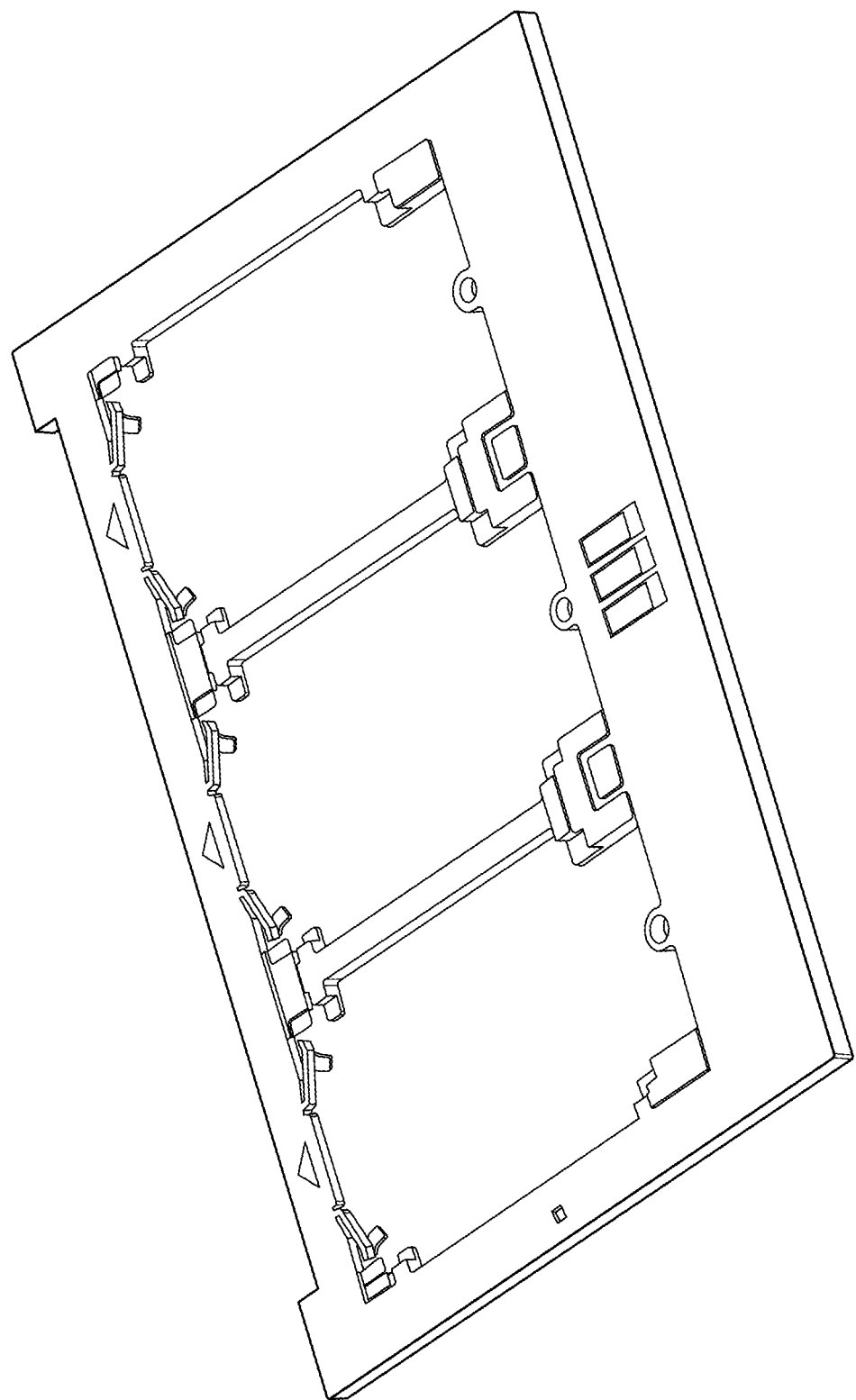
FIG. 3A illustrates a slide tray having three slide positions, in accordance with some embodiments.
Figure 3B:
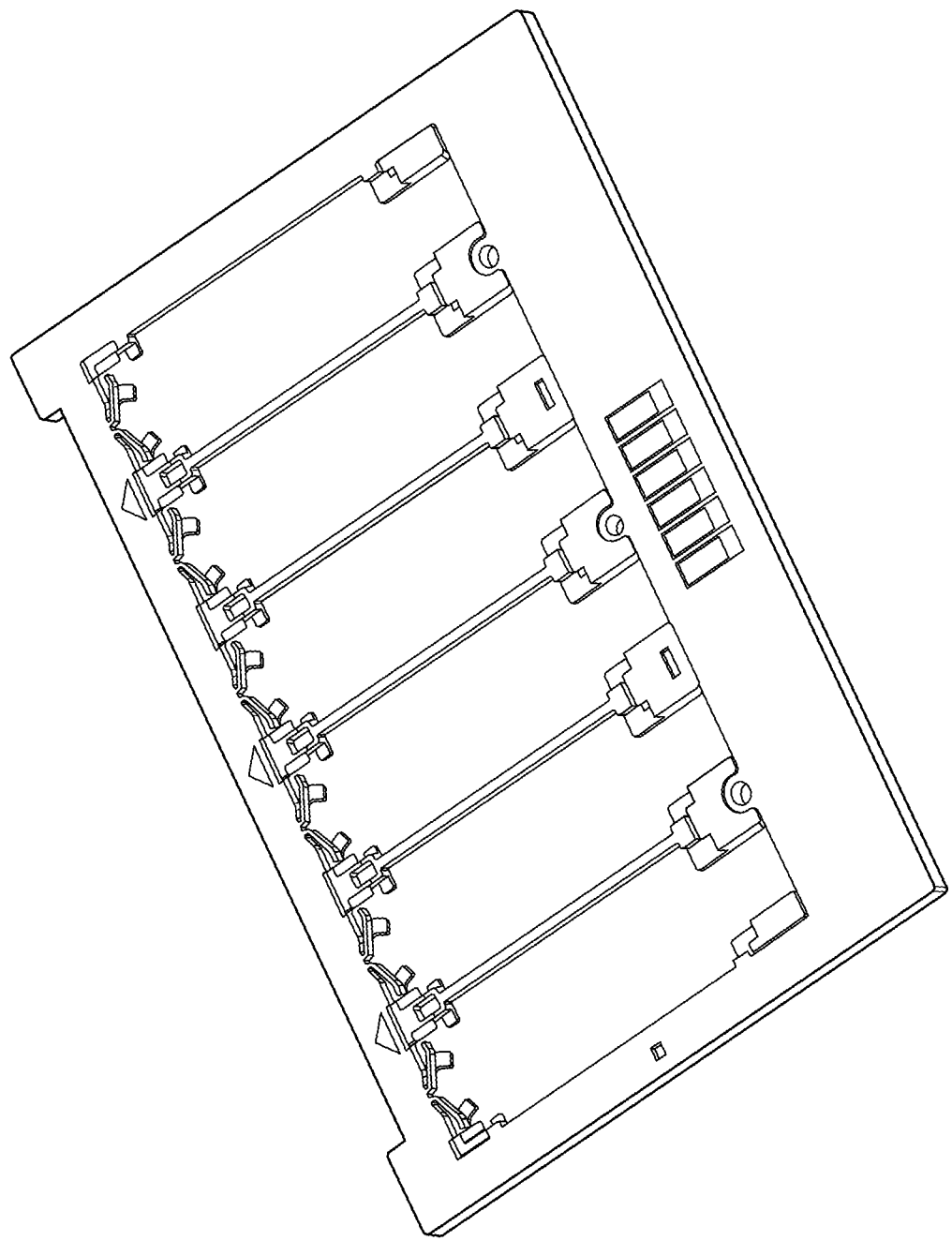
FIG. 3B illustrates a slide tray having six slide positions, in accordance with some embodiments.

In some embodiments, the slide tray includes a plurality of slide positions, each slide position adapted to hold a microscope slide. In some embodiments, the slide tray is configured to hold between 3 and 6 microscope slides. In other embodiments, the slide tray is configured to hold 3 microscope slides (see FIG. 3A). In yet other embodiments, the slide tray is configured to hold 6 microscope slides. (see FIG. 3B).

The skilled artisan will appreciate while a slide tray may hold between 3 and 6 microscope slides, not all of the slide positions need to be occupied with a slide for the slide tray to be inserted into the slide scanning device 110 or for a scanning operation to be undertaken by the slide scanning device 110. By way of example, for a slide tray holding 6 slides, between 1 and 6 of the available slide positions may be occupied with a slide. Likewise, for a slide tray holding 3 slides, between 1 and 3 of the available slide positions may be occupied with a slide. In any event, the skilled artisan will further appreciate that the slide tray facilitates the loading and fast scanning of slides.

Following the receipt of a slide tray insertion signal by the interface module 126 (step 220), the GUI renderer 128 generates a representation of the slide tray, such as to the user interface and visualization on an output device, such as the display 108 (step 221). In some embodiments, the representation generated by GUI renderer 128 is a depiction of the layout of the slide positions in the slide tray. Said another way, the representation displayed mimics the layout of slides arranged in a slide tray. As such, if a slide tray having three slide positions is inserted at step 200, GUI renderer 128 will display a representation having three 3 slide positions, such as three slide positions arranged in parallel relative to each other (see FIG. 4A). Likewise, if a slide tray having six slide positions is inserted at step 200, GUI renderer 128 will provide a representation having six slide positions, such as six slide positions arranged in parallel relative to each other (see FIG. 4B).

In some embodiments, and in addition to the placeholders, the GUI renderer 128 displays a menu bar 404 having user selectable elements which, when selected by the input device 106, may initiate one or more of a scanning operation, area of interest ("AOI") adjustment operations, the launching of a viewer module 134 or view software, etc. In some embodiments, and in addition to the placeholders, the GUI renderer 128 displays a configuration panel 403 providing a plurality of user configurable scanning parameters.

In some embodiments, the representation generated by GUI renderer 128 comprises a plurality of non-overlapping placeholders 400. In some embodiments, each of the plurality of placeholders are equally sized. In some embodiment, the plurality of placeholders are arranged in a vertical orientation, i.e. the long edges of the placeholders are parallel to a displayed capture settings or configuration panel. In some embodiments, each placeholder corresponds to a particular slide position in the slide tray. In this way, the placeholders displayed represent the actual layout of slides in a slide tray. In some embodiments, the placeholders displayed represent the actual shape and size of the slides within the slide tray. In some embodiments, the GUI renderer 128 displays a placeholder 400 for each slide position of a slide tray, regardless of whether the slide tray is occupied with a microscope slide. For example, where a slide tray having six slide positions is inserted into scanning device 110 and where positions 1, 4, and 6 of the physical slide tray are occupied with a slide, the GUI renderer 128 will display six non-overlapping, equally sized placeholders 400, despite positions 2, 3, and 5 not being occupied with microscope slides. In this way, an accurate visualization is depicted within the user interface of the particular slide tray inserted into the slide scanning device 110 including slide positions occupied with biological sample bearing slides, thus facilitating feedback to the user of the scanning system 100.

With reference to FIG. 4A, in some embodiments, each placeholder 400 is adapted to at least convey image data (e.g. a preview scan image, a thumbnail scan, an intermediate scan, a high resolution scan, etc.) received from the scanning device 110 to the user of the scanning system 100 via the displayed user interface. In some embodiments, each placeholder 400 is adapted to convey image data corresponding to a scan of an entire microscope slide, including the microscope slide's label portion (see, for example, FIG. 5D for a whole slide scan). In some embodiments, the label portion may include a bar code or other alphanumeric information or indicia. In some embodiments, the label portion supplies identifying information as to the patient, the case number, the case type, the date the sample was prepared, etc. In some embodiments, the user interface provides a user selectable option or label anonymization feature of hiding the label portion of any slide depicted within a placeholder so as to retain patient anonymity (e.g. an option selectable in a configuration panel). In some embodiments, even where patient data is hidden, the scanning system 100 may automatically retrieve and recognize (e.g. by optical character recognition using OCR/decoder module 132)

some or all of the data encoded within the label portion (including barcode), such as to populate one or more metadata fields, filenames, DICOM file attributes, fillable fields of other medical/imaging industry file formats, etc. In some embodiments, where slide label information is "hidden" through a user command, the slide label information is removed from one or more metadata fields.

In some embodiments, each placeholder 400 generated by GUI renderer 128 includes a first portion 401 and a second portion 402. In some embodiments, the first portion 401 is adapted to convey received image data of a biological sample disposed on a microscope slide (with or without the label portion of the slide). In some embodiments, the second portion 402 is adapted to convey one of more data fields, such as a scanning operation status data field and/or one or more scanning attribute/scanning parameter data fields. In some embodiments, the second portion 402 of any individual placeholder 400 may convey a status of a scanning operation using alphanumeric descriptors, status bars, animated status bars, animations, or other graphics or animated graphics.

Of course, the skilled artisan will appreciate that status indications within the second portion 402 of any placeholder 400 may be color coded. In some embodiments, a first color may represent a first status, a second color may represent a second status, and a third color may represent a third status, where each of the colors are different. In some embodiments, an indication of a scanning operation status may be that no scanning status information is provided. For example, when no slide is located at a particular slide position in a slide tray, the status field may be left blank, indicating that no slide is present. Alternatively, the field remains the same color as the background color of the second portion. Thus, in this particular embodiment, the scanning operation status is that no scanning will be commenced for that particular placeholder/slide position.

In some embodiments, the scanning operation status conveyed in the second portion 402 is synchronized in real-time with status lights/indicator lights present on an exterior surface of the scanning device 110. In some embodiments, and as noted above, the slide scanning device 110 may include an exterior panel having a plurality of status indicator lights, where each status indicator light corresponds to one of the plurality of placeholders 400, which in turn correspond to slide positions in a slide tray. In some embodiments, colored indicia displayed within the second portion 402 of any placeholder 400 within the user interface may be synchronized with the corresponding scanning device status indicator lights such that any color displayed within any second portion 402 of a placeholder 400 may substantially match a color of the corresponding individual status indicator light for the same slide position. Likewise, an animation conveyed within a second portion 402 of any placeholder 400 within the user interface may be mimicked by blinking or flashing the respective status indicator light on the scanning device 110. For example, if a first status indicator light on the scanning device 110 blinks a first color, an area of the second portion 402 of the first placeholder 400 within the user interface may flash or have an animated bar that displays the same first color as the indicator light. In this way, the user of the scanning system 100 receives synchronized visual status indications from both the user interface and the scanning device 110, which is believed to enhance the user experience and facilitate real-time scanning operation feedback.

In some embodiments, signals are transmitted from interface module 126 to the scanning device 110 to initiate one or more scanning operations. In some embodiments, the interface module 126 sends signals to the scanning device 110 to automatically initiate the scanning of slides at one or more slides positions along with a set of predetermined scanning settings (such as a set of scanning settings stored in storage subsystem 104). As such, in some embodiments, upon receipt of the slide tray insertion signal (step 220) and the displaying of the plurality of placeholders (step 221), scanning is automatically initiated using a set of predetermined scanning settings. In other embodiments, upon receipt of the slide tray insertion signal (step 220) and the displaying of the plurality of placeholders (step 221), user input signals are transmitted to the scanning device 110 through the interface module 126 such that scanning may be initiated (manual initiation of scanning). The manual initiation of scanning may utilize preset scanning settings or settings provided through user inputs as noted herein.

Following the displaying of the representation including the plurality of placeholders (step 221), scanning is initiated and subsequently the one or more placeholders 400 are populated with data received from the scanning device 110 or from the scanning interface application 120 (regardless of whether the scanning was initiated automatically or manually, or whether the settings used for scanning were selected manually or based on a preset) (step 222). For example, the scanning device 110 may transmit scanning operation status data and/or may transmit image data, and such information may be populated into the placeholders 400. Additionally, the placeholders 400 may be populated with the scanning settings used in the acquisition of the image data for each slide position (i.e. the stored preset or manually entered scanning settings which were transmitted to the scanning device 110).

In some embodiments, each slide is scanned individually and, as a result, the placeholders 400 are sequentially populated with the scanned image data. In some embodiments, and prior to the population of the placeholders 400 with image data, the placeholders 400 are populated with at least information pertaining to a status of a scanning operation. In some embodiments, and again prior to the population of the placeholders 400 with image data, the placeholders 400 are populated with both scanning operation status information and scanning settings. In some embodiments, all placeholders 400 are populated with status data and/or scanning parameter data substantially simultaneously.

Figure 2C:
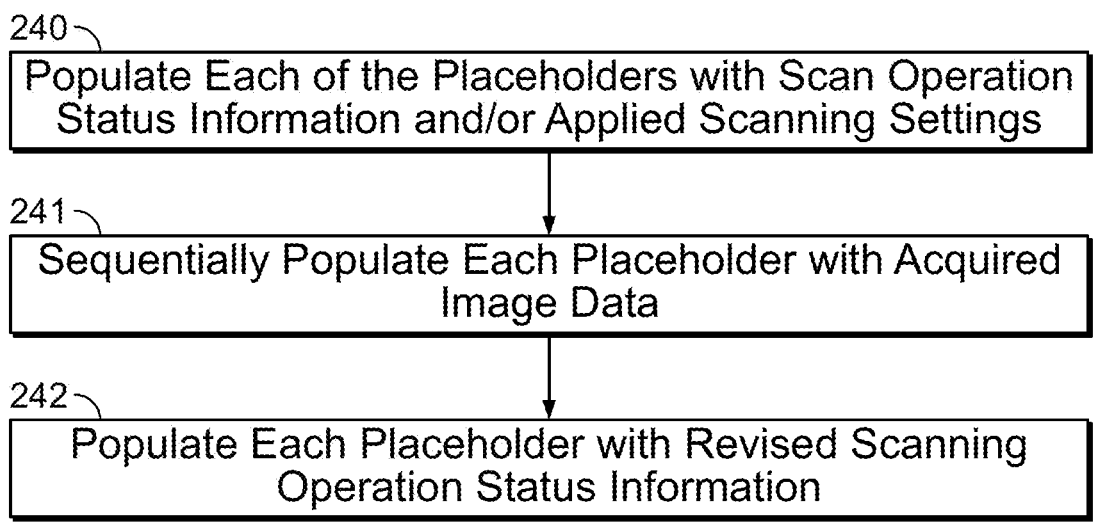
FIG. 2C sets forth a flowchart illustrating the steps of receiving data, such as image data or scanning operation status data, and providing such received data to a user interface so as to facilitate the review of image data and the optional adjustment of scanning settings, in accordance with some embodiments.

With reference to FIG. 2C, in some embodiments, scanning operation status data is transmitted from the slide scanning device 110 separate from the transmission of image data, i.e. each placeholder 400 is initially populated with scanning operation status information and/or scanning settings (step 240), and then populated with image data once scanning of a slide at a slide position corresponding to the placeholder is complete (step 241). For example, when a slide at any slide position is being scanned, scanning operation status information for each slide position is transmitted (step 240) such that the user interface may display, such as in real-time, the scanning operation status within the corresponding placeholder (in conjunction with any contemporaneous status displayed on a slide status panel on the scanning device 110). When the scanning of a slide at any position is complete, the resulting image data is then transmitted from the slide scanning device 110 to the interface module 126 such that the image data may be populated into one of the placeholders (step 241). In addition, new scanning operation status information is provided such that each placeholder displays an updated scanning status (step 242). The skilled artisan will appreciate that scanning status information may be continuously transmitted or updated, such as in real-time, while the scanning device 110 is acquiring scans of the microscope slides present at any slide position. In this way, the status data is continuously supplied to the user as feedback (i.e. step 242 may be repeated as the image data is sequentially populated into placeholders).

Figure 5A:
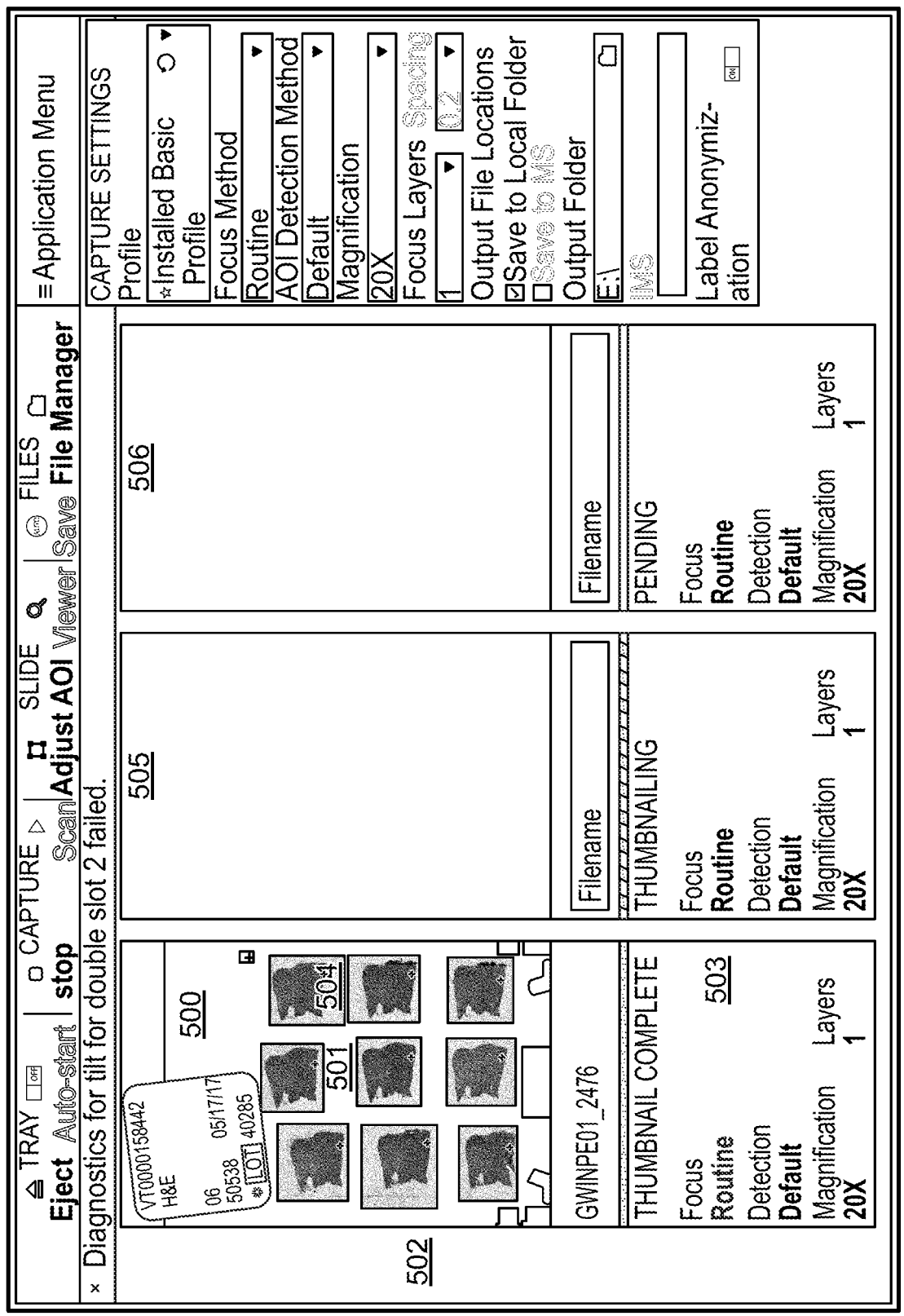
FIG. 5A illustrates a user interface setting forth a representation of a slide tray having three slide positions, the representation including three placeholders; wherein the first placeholder is illustrated as including a thumbnail image scan and an indication that the thumbnail image scan is complete, along with the scanning settings used in generating the thumbnail scan; while the second and third placeholders display scanning operation status information and the scanning settings which are to be utilized in generating the respectively thumbnail image scan and/or high-resolution image scan.
Figure 5B:
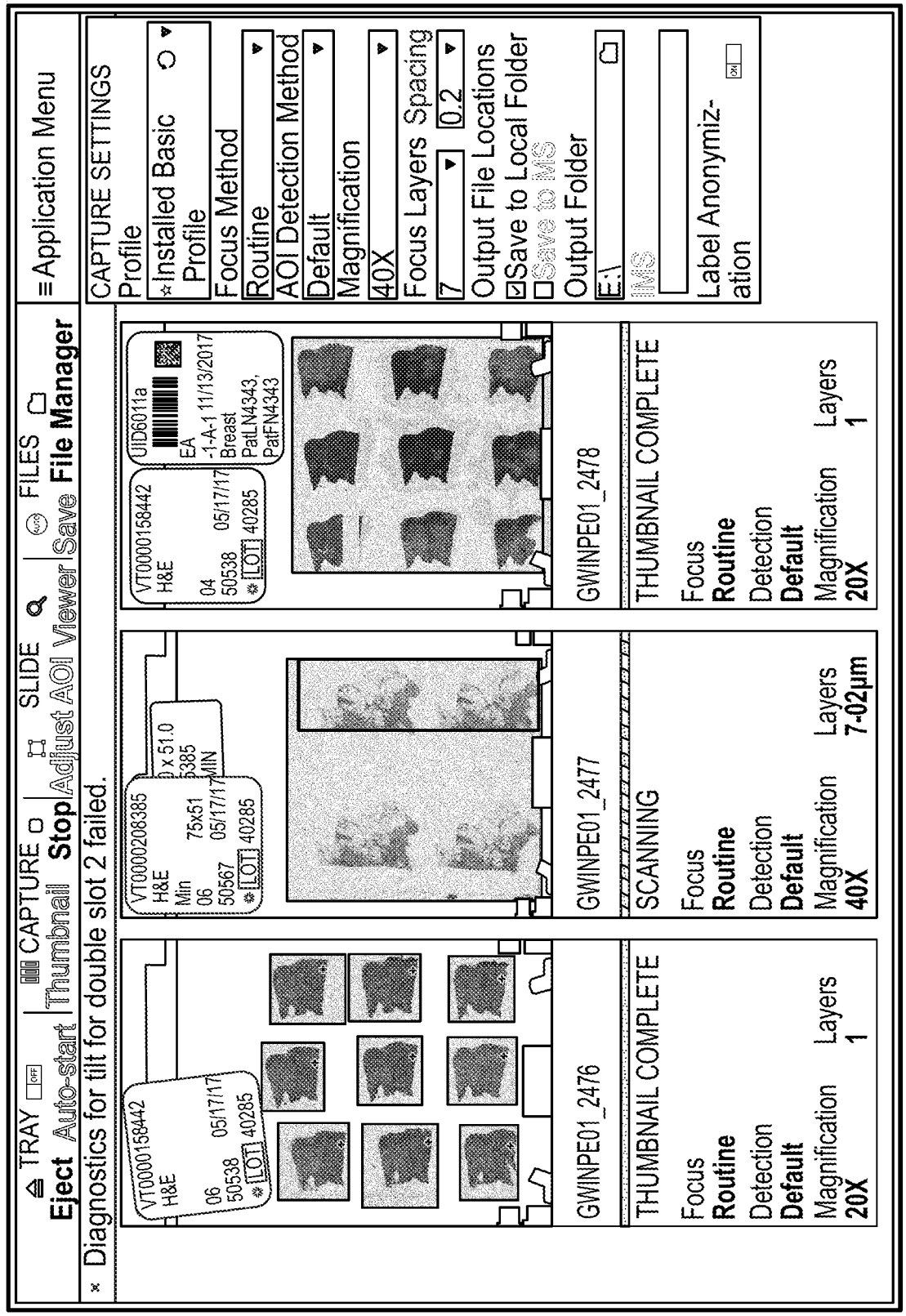
FIG. 5B illustrates a user interface setting forth a representation of a slide tray having three slide positions, the representation including three placeholders; wherein the first placeholder is illustrated as including a thumbnail image and additional information including (i) an indication that the thumbnail image scan is complete, and (ii) the scanning settings used in generating the thumbnail image scan; the second position illustrates another thumbnail image scan, along with an indication that a high-resolution image is being actively scanned along with the scanning settings being utilized in the scanning operation; and the third placeholder illustrates that a thumbnail scan is complete, along with the thumbnail image data and scanning settings utilized in generating the scan, in accordance with some embodiments.
Figure 5C:
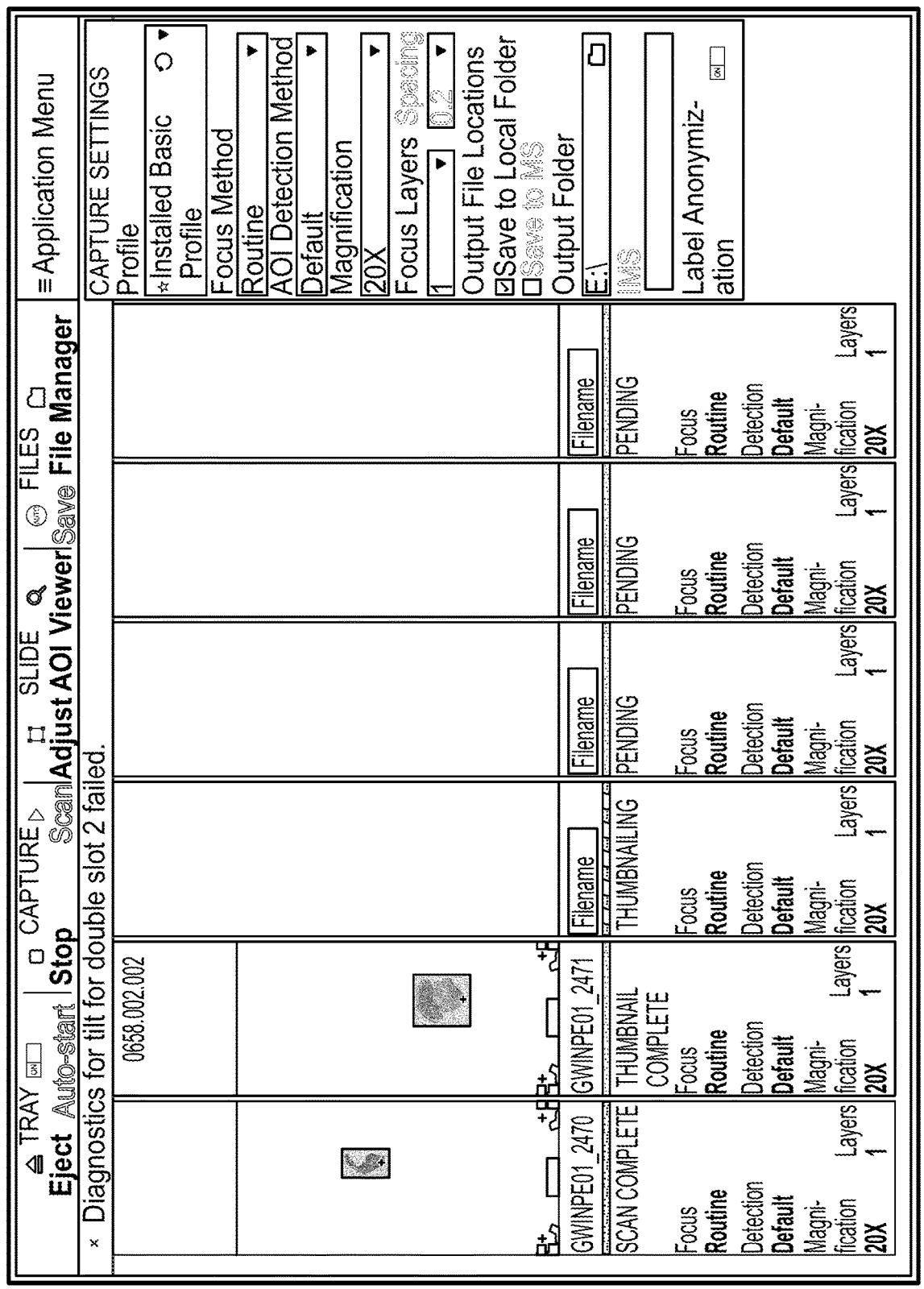
FIG. 5C illustrates a user interface setting forth a representation of a slide tray having six slide positions, the representation including six placeholders; wherein the first placeholder is illustrated as including a thumbnail image and an indication that a high-resolution image scan is complete, along with the scanning settings used in generating the high-resolution image scan; the second placeholder illustrates that a thumbnail scan is complete, along with the thumbnail image data and scanning settings utilized in generating the thumbnail image scan; the third, fourth, fifth, and sixth placeholders display scanning operation status information and the scanning settings which are to be utilized in generating the thumbnail image scans and/or high-resolution image scans, in accordance with some embodiments.
Figure 5D:
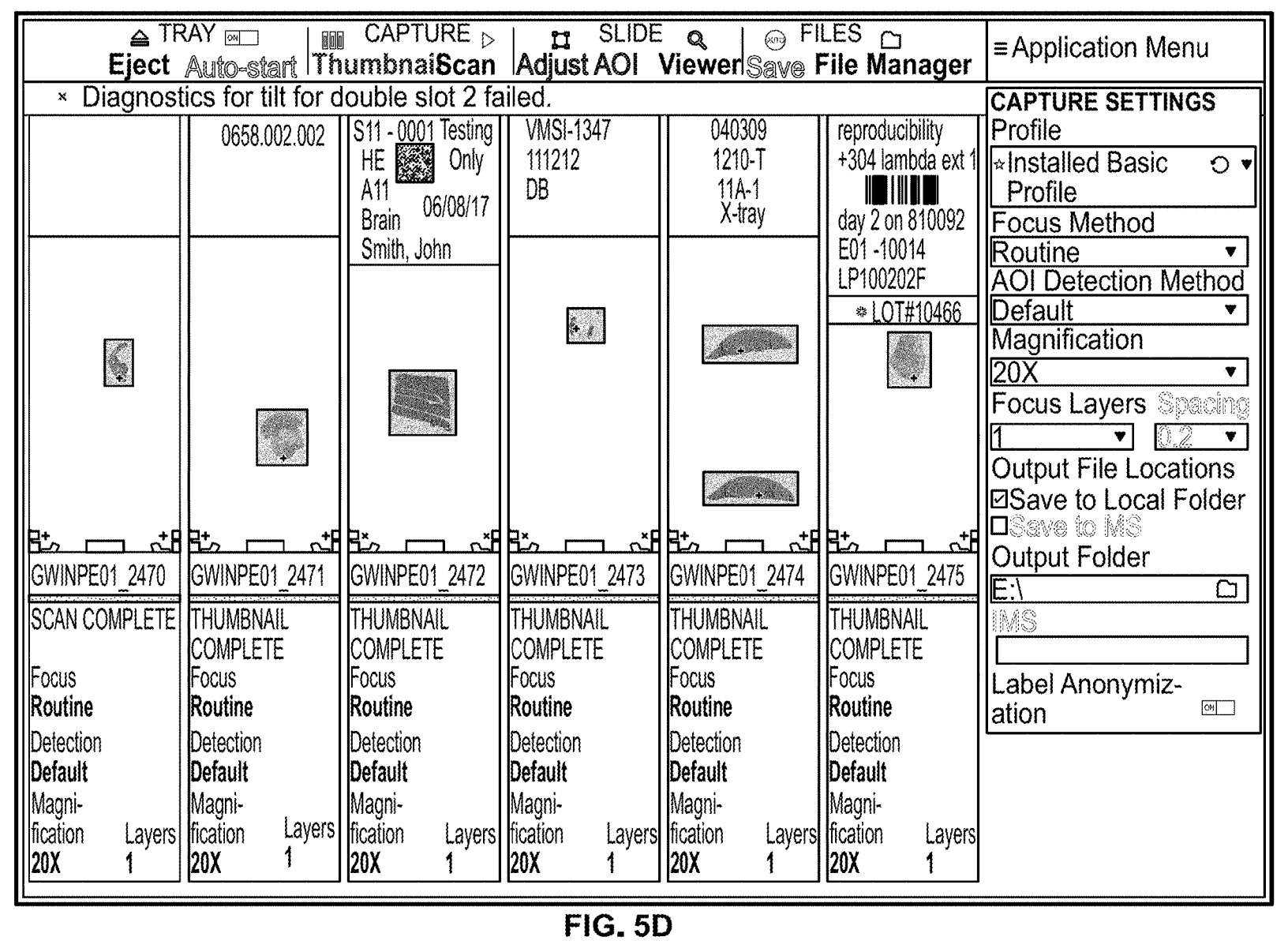
Figure 5E:
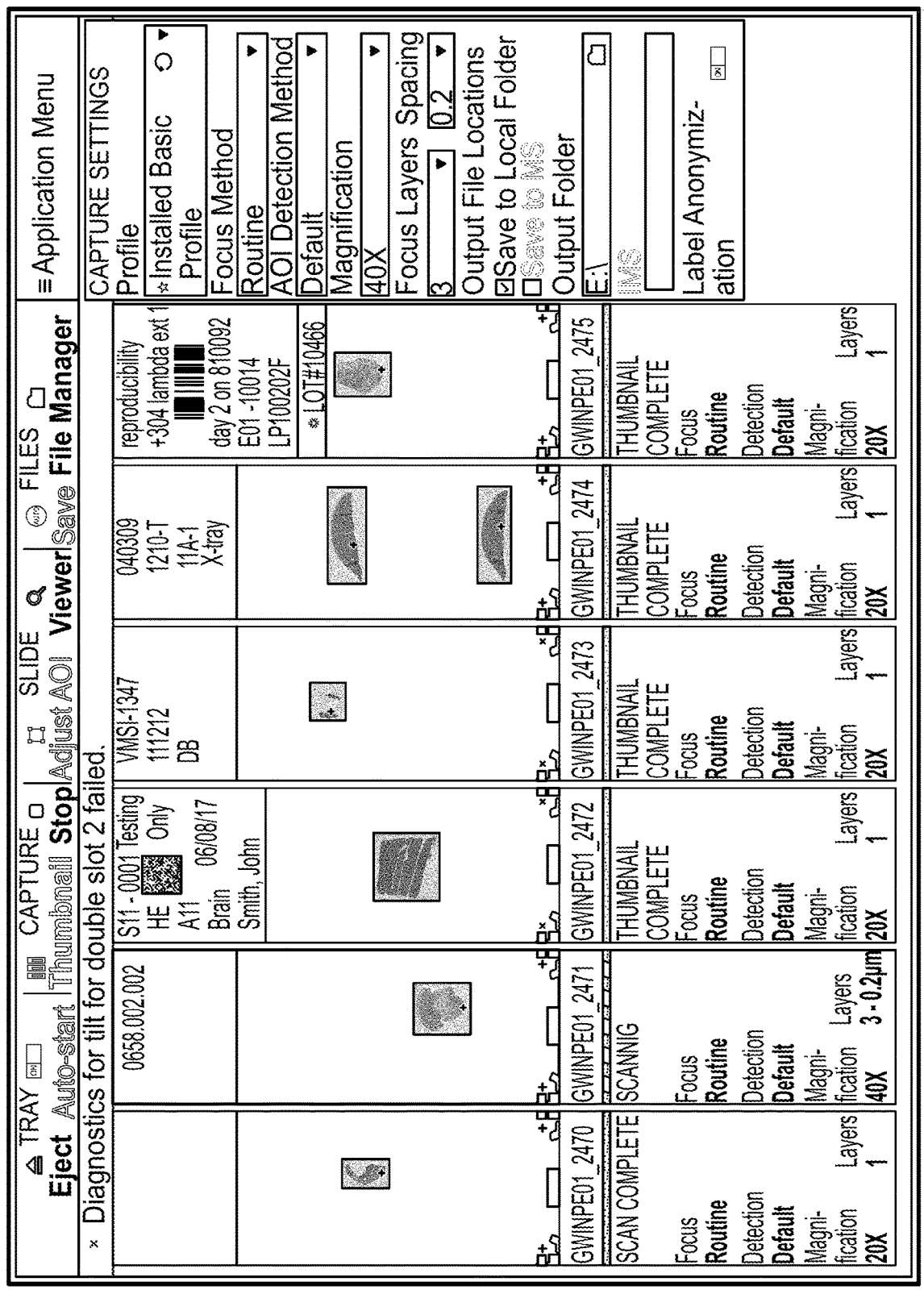
FIG. 5E illustrates a user interface setting forth a representation of a slide tray having six slide positions, the representation including six placeholders, where all six placeholders include thumbnail image scans and scanning operation statuses. Notably, the second placeholder indicates that scanning is commencing (i.e. a high-resolution image scan is being generated) based on selected scanning settings (e.g. the selection of 40× magnification and multiple focus layers spaced 0.2 microns apart), in accordance with some embodiments.

By way of example, suppose a slide tray having six slide positions is inserted into the scanning device 110. Suppose further that slide positions 1, 2, 4, 5, and 6 are occupied with microscope slides bearing different biological samples. After the placeholders 400 are displayed within the user interface, at least scanning operation status signals are transmitted from the slide scanning device 110 such that the status of a scanning operation may be displayed for each of slide positions 1, 2, 4, 5, and 6. In some embodiments, and in addition to the scanning operation status signals, each placeholder 400 is populated with an identification of the scanning settings being used by the scanning device 110 in acquiring the respective image data. By way of further example, as the slide at position 1 is being scanned, the second portion of the first placeholder may provide indicia indicating that slide 1 is "scanning," while the second portions of each of the second, fourth, fifth, and sixth placeholders may provide indicia indicating that slides 2, 4, 5, and 6 are "pending." Of course, and as noted above, the status indicator lights on the exterior of slide scanning device 110 may simultaneously portray the same status indicia for each of the slide positions. FIGS. 5A and 5B are illustrative of the sequential population of the placeholders with image data. Similarly, FIGS. 5C and 5D are also illustrative of the sequential population of the placeholders with image data and/or scanning operation status datainformation. FIG. 5E, as compared with FIG. 5D, illustrates the initiation of a high-resolution scan using selected user configurable scanning settings (see the second placeholder in each figure).

Taking the above example further, when scanning of the first slide is complete, the second portion of the first placeholder may provide indicia that the scanning is complete, and different indicia may be provided depending on whether the image data acquired was a thumbnail image (i.e. a low resolution image suitable for reviewing the AOI and capture or scanning settings for the tissue section) or a high-resolution image (e.g. a 20× or 40× magnification scan of the slide). The second portions of the second, fourth, fifth, and sixth placeholders will likewise convey different status indicia after the scanning of the first slide is complete and the scanning of the second slide commences (e.g. first position=scanning complete; second position=scanning; fourth position=pending; fifth position=pending; and sixth position=pending). Concomitant changes to the status indicator lights on the exterior of the scanning device 110 will also be provided.

As illustrated in FIG. 5A, after scanning is complete for one of the slides at any slide position, the user interface will provide scanned image data 501 (the image data may be a low resolution or high-resolution capture) in a first portion 502 of a placeholder 500 and a scanning operation status indication and/or scanning parameters in a second portion 503 of placeholder 500. As noted herein, the scanning settings displayed reflect those scanning settings which were applied during acquisition of the image data populated in the placeholder (regardless of the scanning settings were manually selected or whether a predetermined set of scanning settings stored on the storage subsystem 104 were utilized). In some embodiments, an automatically generated AOI 504 (or, as is the case in FIG. 5A, a plurality of AOIs) is superimposed over the image data 501 (see blue, rectangular boxes around each portion of the stained tissue on the scanned microscope slide).

The skilled artisan will appreciate that while one of the placeholders may be populated with image data (e.g. a preview scan), scanning of slides to generate image data for population into other placeholders may be commencing and or be scheduled (e.g. placeholder 505 in FIG. 5A indicates that a scan is being acquired, while placeholder 506 indicates that a scan is scheduled and therefore "pending"). The skilled artisan will also appreciate that while other scans are pending or scheduled, the user may view the image data and/or make adjustments to the scanning settings used to acquire the image data displayed. Said another way, the user does not have to wait until all placeholders are populated with image data to view any particular image or make adjustments to scanning settings, including AOI parameters.

After the image is displayed in one of the placeholders, the user may review the image data, the scanning parameters, and/or any pre-computed AOI and make an informed decision, based on the totality of data presented, at least within the user interface workspace, as to whether the scanning parameters require adjustment (step 223). In some embodiments, a viewer module 134 or other viewer software provided within storage subsystem 104 may be executed by the processing subsystem 102 to further aid the user in the determination as to whether scanning parameters need adjustment. As noted herein, a viewer module 134 may, in some embodiments, be executed to facilitate viewing of regions or portions of the scanned image data, such as a magnified portion of the image.

Figure 2D:
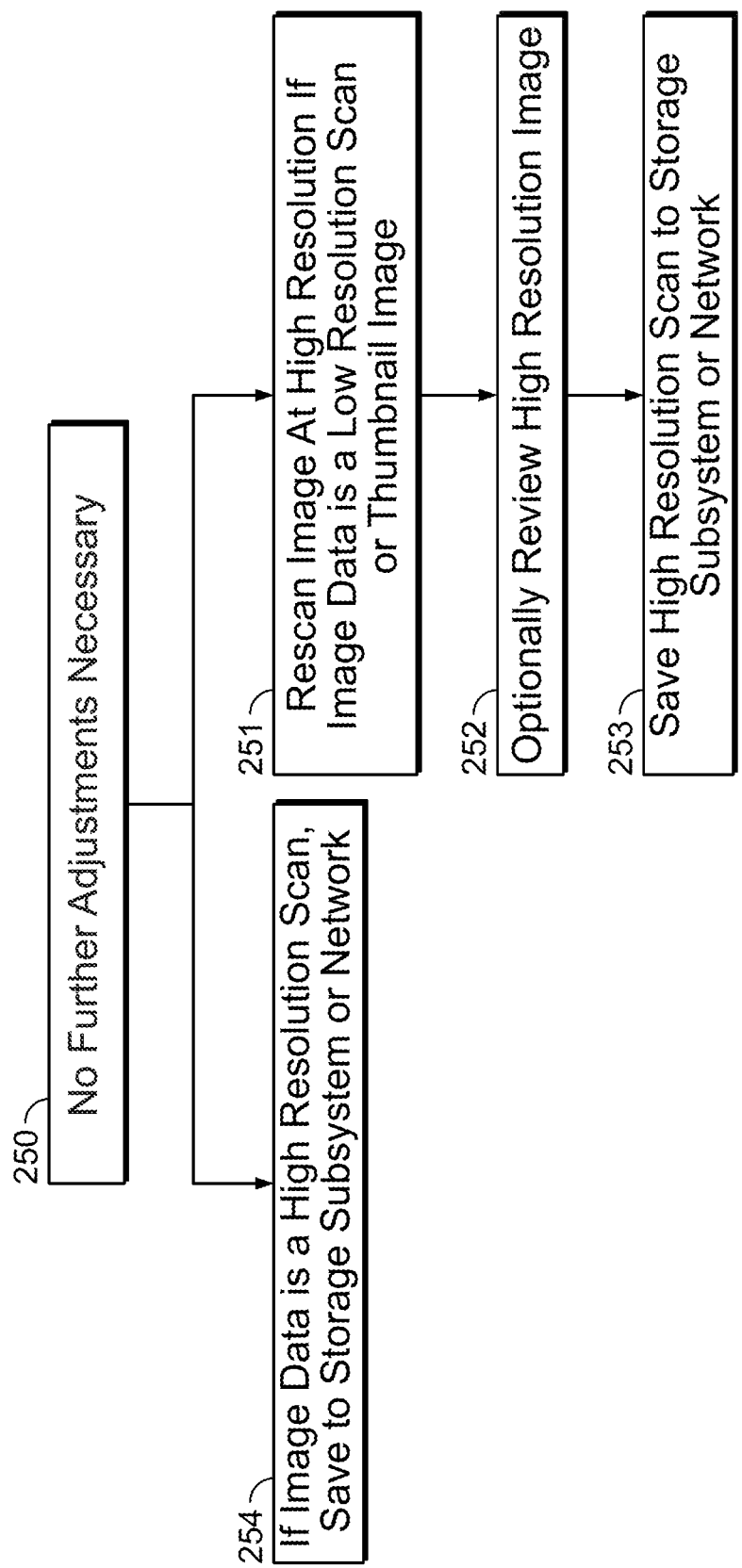
FIG. 2D sets forth a flowchart illustrating the steps of determining, such as via a user interface, whether image data meets predetermined criteria, and the steps of adjusting scanning settings via a user interface and storing any generated high-resolution scan, in accordance with some embodiments.

With reference to FIG. 2D, in some embodiments, no further adjustments are needed (step 250). In the instance that a high-resolution scan was taken at the same time as a thumbnail image was acquired (i.e. the image data in the placeholder is a thumbnail image, but a high-resolution can was conducted contemporaneously), the high-resolution image may be saved (steps 254 or 224) to the storage subsystem 104 or to a network (in one of a variety of different file formats, including the DICOM format). If only a low-resolution image or thumbnail image was acquired, then user inputs may be provided such that a high-resolution scan is acquired using the same scan settings in which the preview scan image was acquired (step 251). Once acquired, the high-resolution scan may optionally be reviewed (such as with a viewer module) (step 252), and then the high-resolution scan may be stored on the storage subsystem 104 or on a network.

Figure 2E:
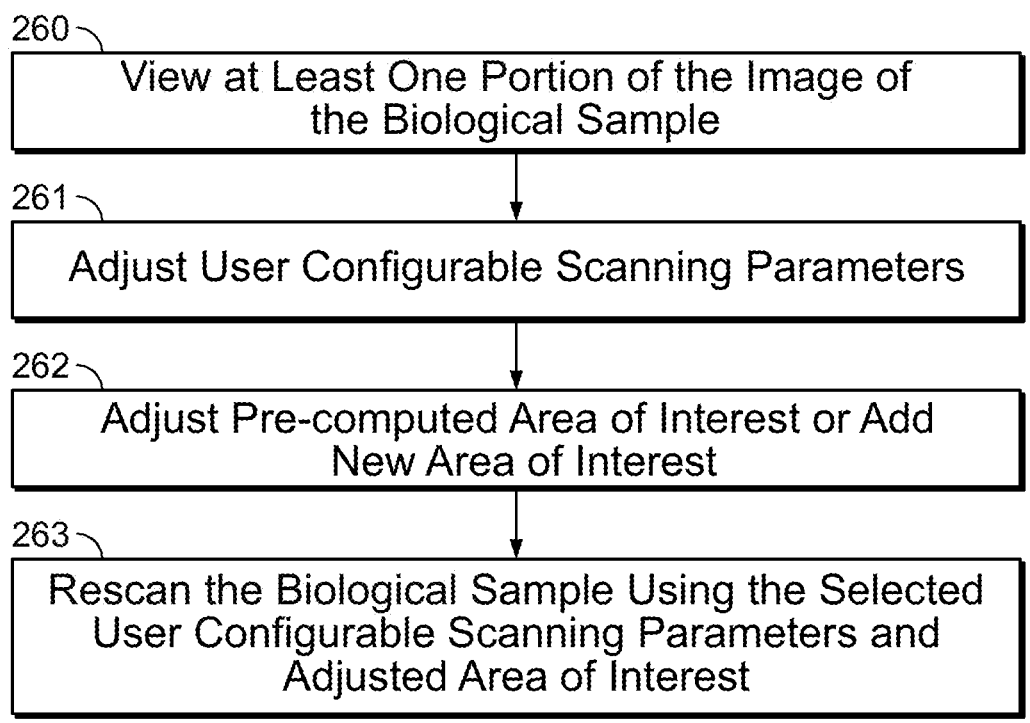
FIG. 2E sets forth a flowchart illustrating the steps of modifying user configurable scanning parameters and/or pre-computed areas of interest, and subsequently rescanning a sample using the selected user configurable scanning parameters and/or modified areas of interest, in accordance with some embodiments.

Alternatively, adjustments may be made to the user configurable scanning parameters and/or the pre-computed AOI and another scan may be generated using the selected and/or adjusted settings (step 225). With reference to FIG. 2E, in some embodiments, a viewer module 134 or other viewer software is used to review at least a portion of an image in one of the placeholders (step 260). For example, the user may be able to determine if an image is out of focus or whether the contrast of the acquired image is inadequate. In some embodiments, input device 106 may be used to position crosshairs on an area of a scanned image such that the spot selected will be displayed in a viewer window.

In some embodiments, the user may select certain user configurable scanning parameters (step 261) which will be applied when rescanning the biological sample. One user configurable scanning parameter is a focus method. In some embodiments, image quality can be maintained for difficult-to-scan samples by adjusting the swathe width. In some embodiments, focus options are available, including those based on a dynamic tracking approach. In other embodiments, a focus method which measures the focus quality and dynamically adjusts the focus as necessary while scanning an AOI may be selected. In yet other embodiments, a focus method may be selected which compensates for tissue variability (e.g. tissue having variable thickness or folds).

In some embodiments, the user may select a user configurable scanning parameter relating to an AOI detection method. For example, a setting may be selected for detecting AOIs for microarrays and disperse samples. Another setting may be selected for detecting AOIs that are round or circular in nature. In other embodiments, a setting may be selected for slides with low contrast samples, such as lightly stained tissues or negative controls. In some embodiments, an AOI detection method may be automatically selected based on attributes encoded within a barcode or other indicia present on the slide. For example, the barcode may contain information pertaining to an assay type or tissue type, and a detection method may be automatically selected that would best determine an area of interest based on the assay type or tissue type.

In some embodiments, the user may select a user configurable scanning parameter relating to a magnification. In some embodiments, 20× and 40× options are made available. It is believed that the digital image produced from each magnification has a resolution similar to that obtained with an optical microscope, when viewing a sample using a 20× or 40× objective.

In some embodiments, the user may select a user configurable scanning parameter such that multiple focus layers may be scanned, e.g. for volume scanning. In some embodiments, a focus layer refers to a plan in the z-axis, which is imaged. In other embodiments, elements are provided within the user interface allow a selection of from between 1 and 15 focus layers. In other embodiments, elements are provided within the user interface allow a selection of from between 3 and 15 focus layers. In some embodiments, elements are provided within the user interface that allow for a selection of the spacing between focus layers, e.g. 0.1 microns, 0.2 microns, 0.25 microns, 0.5 microns, and 1.0 micron.

As noted herein, a user configurable feature within the user interface, such as within a scan settings panel, may also be selected such that information in a label portion may be "hidden" or anonymized. By selecting such a label anonymization feature, bar codes and other identifying information on a label portion of the slide, and depicted within the first portion of any placeholder, may be masked out (either permanently or masked from the view of the user of the scanning system 100). In some embodiments, even if this data is hidden, metadata may be able to be collected and used to populate fields, such as DICOM image attributes.

The user configurable scanning settings may be applied to one, all, or any subset of placeholders. By "applied to a placeholder," it is meant that upon rescanning of a sample at one, all, or any subset of the slide positions, any resulting scan will have been acquired using the selected user configurable scanning settings. For example, the user may be able to select one, all, or multiple placeholders and the user configurable scanning settings may be applied to each placeholder selected to further facilitate ease of use, speed of scanning slides, and intuitive operation of the system.

In some embodiments, the user interface includes an element that, when selected via the user input device 106, enables the adjustment of a pre-computed AOI (step 262). As described herein, the pre-computed AOI is superimposed over the image in the placeholder. The pre-computed AOI may be represented by, for example, a colored box (see 504 of FIG. 5A). The colored box may be resized, moved, or deleted through the use of input device 106, such as in real-time. For example, by clicking with input device 106 and holding a 4-way move pointer inside of the pre-computed AOI, a user may drag the AOI to the desired location on the slide, after which the scanning interface application 120 determines a new focus point on the tissue section (where the focus point is a starting location for a scan, and it may be automatically selected or user determined). In some embodiments, a superimposed focus point may also be moved through the use of input device 106. While it is believed that the focus point can be manually moved to optimize scanning, it should preferably be located somewhere on the tissue. It is believed that the optimal location for the focus point is on the longest section of the tissue near the bottom. In some embodiments, such as for disperse samples, the focus point should preferably be located in a region of greatest density near the bottom of the tissue. Likewise, the input device 106 may be used to add one or more new AOIs.

Following the selection of user configurable scanning parameters and/or adjustments to the pre-computed AOIs, the biological sample is rescanned using the selected parameters (steps 263 and 225). Following rescanning, a determination may again be made as to whether the settings applied were satisfactory (step 226) and, if so, a high-resolution image may be stored (step 227) within the storage subsystem 104 or on a network. The skilled artisan will appreciate that steps 260 through 263 may be repeated as many times as necessary until a suitable scan is acquired, i.e. a scan is acquired meeting pre-determined criteria. When images have been stored for each slide position bearing a sample, the slide may be ejected through the selection of an appropriate user interface element (e.g. an "eject" icon). The scanning system 100 may then be prepared for scanning another set of slides.

In some embodiments, the user interface may provide additional feedback to the user. For example, the GUI rendered 128 may provide overlays within the user interface, such as overlays indicating a scanning error, etc. In some embodiments, the overlays may be presented in a color, e.g. red, where user attention is necessary.

Figure 6:
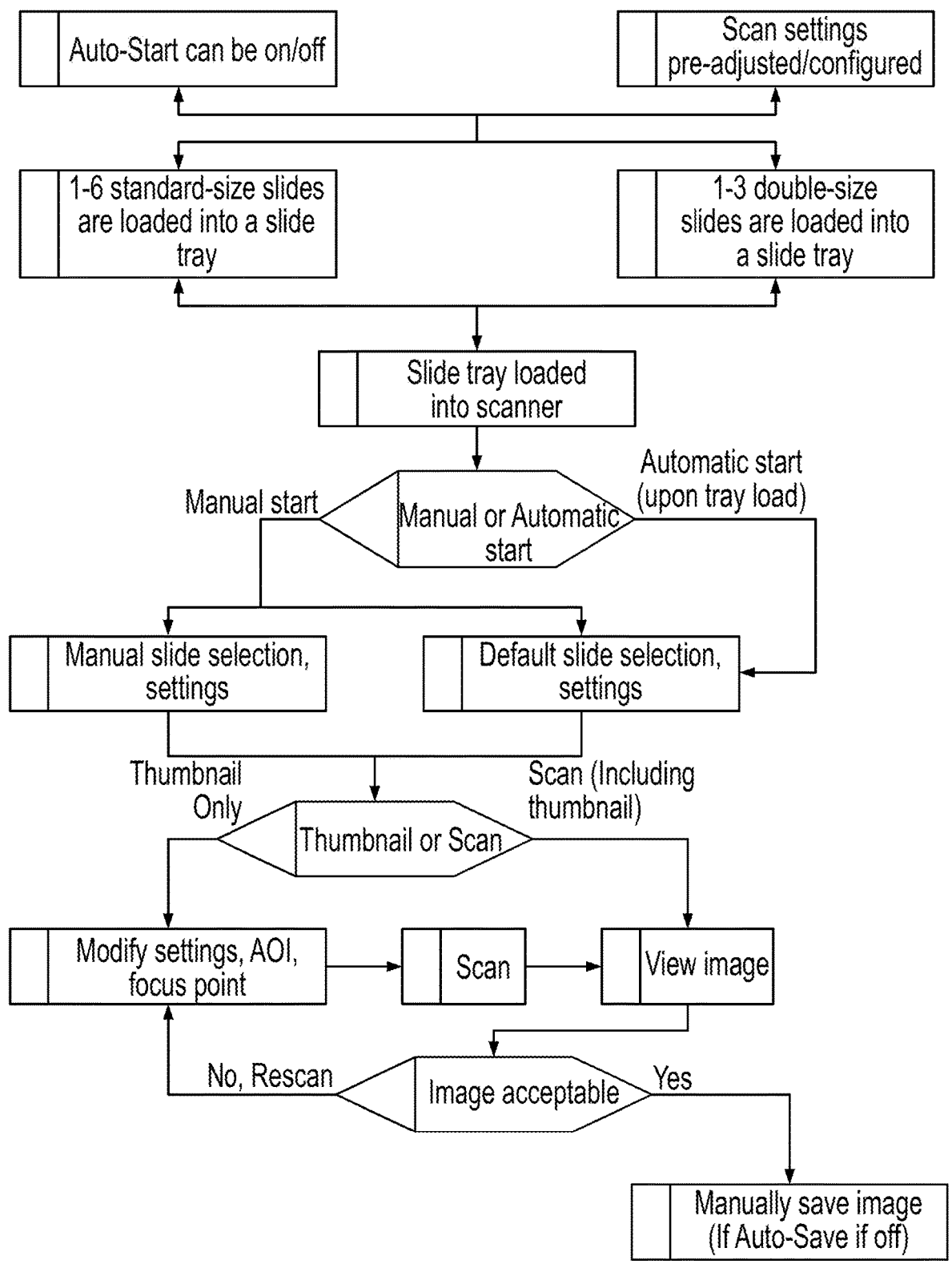
FIG. 6 sets forth a workflow indicating the various steps of generating a high-resolution scan of a biological sample disposed on a substrate (e.g. a microscope slide), the steps including receiving signals that a substrate has been received by the scanning device, sending signals to initiate a scan, receiving scan data (including image and status data), displaying the image data; sending signals to initiate rescanning based on selected scanning settings, and/or sending signals to store the generated high-resolution image scans, in accordance with some embodiments.

FIG. 6 provides another flow chart illustrating the steps of acquiring a high-resolution image using scanning device 110. In particular, FIG. 6 illustrates that the initiation of scanning can be manual or automatic, as detailed herein. If initiation of scanning is set within the scanning interface application 120 to be automatic, predetermined scanning settings are applied during scanning. However, if scanning is initially manually, such as by selecting an element within the user interface that causes a signal to be sent to the scanning device 110 to initiate scanning, scanning settings may be set manually or predetermined scanning settings may be applied. If the scanning settings are set manually, a plurality of user configurable scanning settings may be displayed by the user interface. Upon their selection, the user configurable scanning settings are applied and used to acquire the initial image data. In some embodiments, the manually applied user configurable scanning settings may be stored as a preset within storage subsystem 104 for later use.

Figure 7:
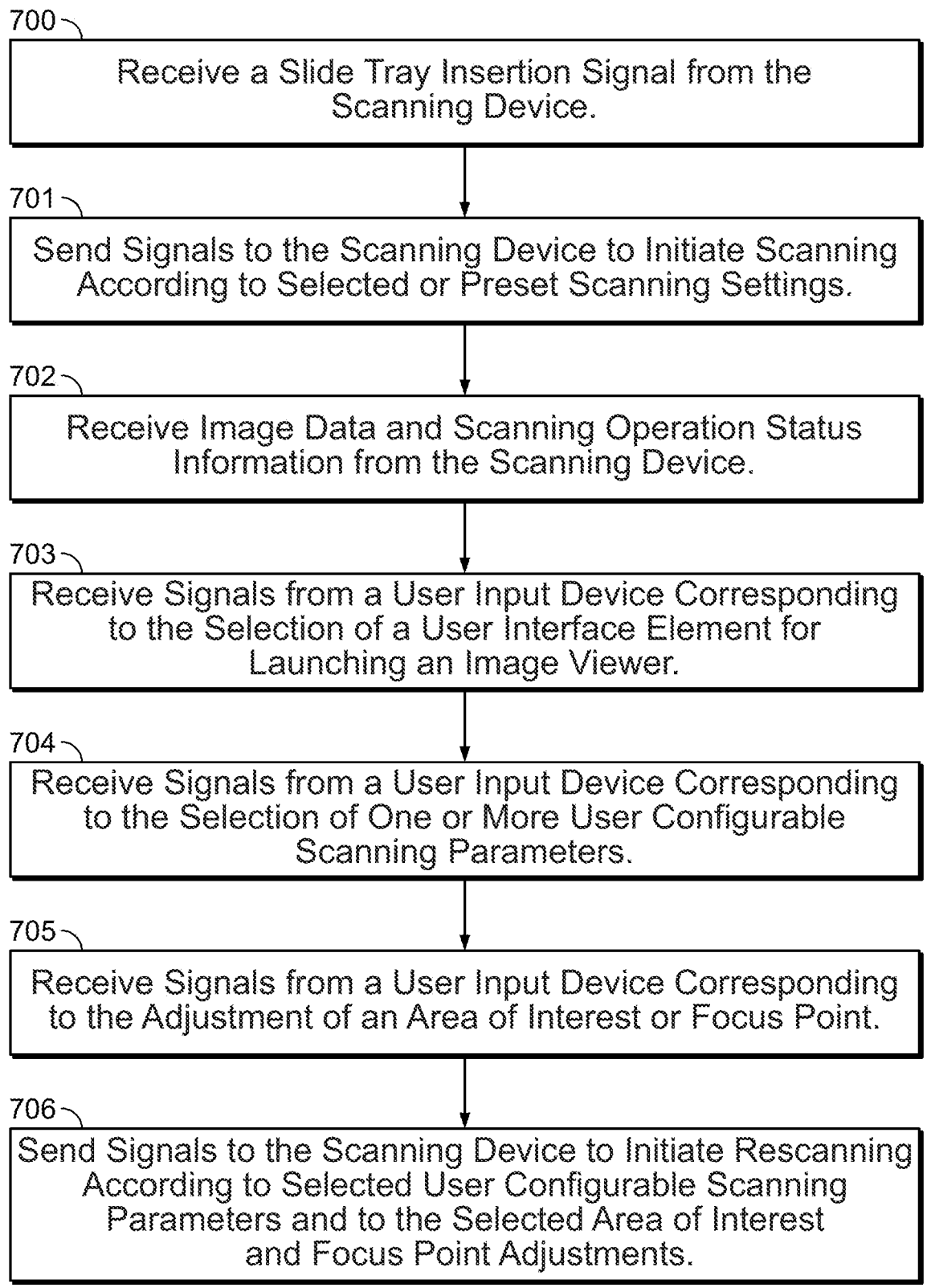
FIG. 7 provides a flow chart illustrating the signals sent to and received from the scanning device and/or input device, in accordance with some embodiments.

FIG. 7 provides a flow chart illustrating the signals sent to and received from the scanning device and/or input device. For example, a slide tray insertion signal is received from the scanning device 110 at step 700. Thereafter, the processing subsystem may display a user interface including a representation of the inserted slide tray. As noted herein, the representation may include a plurality of placeholders where image data, scanning operation status information and/or scanning settings may be conveyed. Following receipt of the slide tray insertion signal (step 700), signals are sent to the scanning device 110 to initiate scanning (step 701). The initiation of scanning may be manual or automatic as noted herein and may utilize selected scanning settings or present scanning settings. Subsequently, image data and scanning operation status information is received from the scanning device 110 (step 702), and such data and information may be populated into the plurality of placeholders within the user interface. In some embodiments, signals are received from an input device 106 corresponding to the selection of a user interface element to launch an image viewer (e.g. viewer module 134 or an external viewer software package) (step 703). After a portion of the image data is reviewed, signals are received corresponding to the selection of one or more user configurable scanning settings (step 704), and/or signals are received corresponding to the adjustment of an area of interest or a focus point (step 705). In some embodiments, the signals corresponding to the selection of one or more user configurable scanning parameters or the to the adjustment of an area of interest or a focus point are then sent to the scanning device 110 such that image data may be rescanned according to the selected scanning settings (step 706).

Additional Embodiments

In some embodiments is a method of acquiring a high-resolution scan of a biological sample disposed on a substrate with a scanning device, the method comprising: (i) receiving, on a graphical user interface, a first user input corresponding to user configurable scanning settings; (ii) receiving, on a graphical user interface, a second user input to initiate scanning based on the received series of user inputs corresponding to user configurable scanning settings; and (iii) displaying, on the graphical user interface, a visualization of one or more placeholders populated with scanning operation status information, image data, and at least a portion of the user configurable scanning settings. In some embodiments, the method further comprises receiving a third user input to store the image data. In some embodiments, the storing of the image data further comprises generating a high-resolution scan of the image data prior to storage. In some embodiments, the method further comprises receiving a fourth user input to rescan image data based on a revised series of user inputs correspond to user configurable scanning settings. In some embodiments, the one or more selected user configurable scanning settings comprise (i) adjustments to a pre-computed area of interest; and (ii) user configurable scanning parameters. In some embodiments, the adjustments to a pre-computed area of interest include resizing an area of interest, repositioning an area of interest, repositioning a focus point, creating a new area of interest, or deleting an area of interest. In some embodiments, the user configurable scanning parameters include a focus method, an area of interest determination method, a magnification, a number of focus layers, and a spacing of focus layers. In some embodiments, the user configurable scanning parameters further include a label anonymization feature.

In some embodiments is a method of acquiring a high-resolution image of a biological sample with a slide scanning device, comprising: (i) displaying a plurality of placeholders, each placeholder corresponding to a slide position of a slide tray inserted in the slide scanning device; (ii) populating the second portion of each of the plurality of placeholders with at least scanning operation status information; (iii) populating the first portion of at least one of the plurality of placeholders with a preview scan image of the biological sample located at the corresponding slide position of the slide tray. In some embodiments, the method further comprises evaluating whether the preview scan image within the at least one of the plurality of placeholders meets predetermined criteria. In some embodiments, the method further comprises generating at least one revised scanned image (e.g. an image having a higher resolution than the preview scan image) based on received input signals corresponding to the selection of one or more user interface elements. In some embodiments, each placeholder has a first portion adapted to convey image data, and a second portion adapted to convey one or more data fields. In some embodiments, the preview scan image is a thumbnail image and the revised scanned image is a high-resolution image. In some embodiments, the user interface element selected is an element which causes the scanning device to initiate a scanning operation.

In some embodiments, the at least one revised scanned image is generated based on received input signals corresponding to one or more selected user configurable scanning settings. In some embodiments, the one or more selected user configurable scanning settings comprise (i) adjustments to a pre-computed area of interest; and (ii) user configurable scanning parameters. In some embodiments, the adjustments to a pre-computed area of interest include resizing an area of interest, repositioning an area of interest, repositioning a focus point, creating a new area of interest, or deleting an area of interest. In some embodiments, the user configurable scanning parameters include a focus method, an AOI detection method, a magnification, a number of focus layers, and a spacing of focus layers. In some embodiments, the user configurable scanning parameters further include a label anonymization feature.

In some embodiments, each of the plurality of placeholders are sequentially populated with preview scan images of the biological sample at the corresponding slide positions of the slide tray. In some embodiments, the scanning operation status information is updated in real-time. In some embodiments, both scanning operation status information and initial scanning parameters are displayed in the second portion of each of the plurality of placeholders.

In some embodiments, an area of interest is superimposed over the preview scan image populated into the first portion of the at least one of the plurality of placeholders. In some embodiments, the placeholders are non-overlapping and equally sized. In some embodiments, three placeholders are displayed. In some embodiments, six placeholders are displayed.

In some embodiments, the biological samples are stained with a primary stain, e.g. H&E. In some embodiments, the biological samples are stained for the presence of a particular biomarker. In some embodiments, the biological samples are stained with a primary stain and also stained for the presence of a particular biomarker.

In some embodiments, the scanning operation status information populated in the second portion of the placeholder is (i) an empty status field, or (ii) a status field which matches a user interface background color, when no slide is present in the corresponding position in the slide tray. In some embodiments, the scanning operation status information populated in the second portion of the placeholder is an alphanumeric entry indicating that no slide is present in the corresponding position in the slide tray.

In some embodiments, the preview scan image populated into the first portion of the at least one of the plurality of placeholders is automatically generated. In some embodiments, the automatically generated preview scan image is acquired using pre-programmed scanning settings, such as pre-programmed scanning settings stored in a presets file on a storage subsystem. In some embodiments, the pre-programmed scanning settings include at least one of a focus method or an area of interest detection method.

In some embodiments, the scanning operation status information includes at least one of alphanumeric indications, animations, and colored indicia. In some embodiments, the slide scanner device includes an exterior panel having a plurality of status indicator lights, each status indicator light corresponding to one of the plurality of placeholders, and wherein the colored indicia displayed for any individual placeholder of the plurality of placeholders substantially matches a color of the corresponding individual status indicator light. In some embodiments, an adjacent pair of slide status indicator lights correspond to a single placeholder.

In some embodiments, the method further comprises automatically recognizing slide label information and populating the slide label information into one or more metadata fields. In some embodiments, the slide label information is embodied within a barcode. In some embodiments, the one or more metadata fields are DICOM attributes. In some embodiments, at least one user configurable scanning setting is automatically changed based on the automatically recognized slide label information, e.g. assay type, tissue type, etc.

In some embodiments, the evaluation of the preview scan image comprises reviewing at least one magnified portion of the preview scan image, such as for focus quality or image contrast. For example, the user may be able to determine if an image is out of focus or whether the contrast of the acquired image is inadequate according to his preferences and/or assay or protocol requirements. In some embodiments, the evaluation takes into consideration the scanning settings utilized in acquiring the preview scan image. In some embodiments, the method further comprises evaluating the revised scanned image, e.g. evaluating a high-resolution image.

In some embodiments, the method further comprises selecting a user control element to initiate a manual scan. In some embodiments, the manual scan utilizes preset scanning settings. In some embodiments, the manual scan utilizes manually selected user configurable scanning settings. In some embodiments, the method of manual scanning further comprises displaying a plurality of user configurable scanning settings, the user configurable scanning settings being independently applicable to one, all, or any subset of placeholders.

In some embodiments is a system for generating high-resolution image scans, the system comprising: (i) one or more processors, and (ii) a memory coupled to the one or more processors, the memory to store computer-executable instructions that, when executed by the one or more processors, cause the system to perform operations comprising: displaying a representation of a slide tray having a plurality of slide positions, wherein the representation includes a plurality of placeholders, each placeholder each corresponding to one of the plurality of slide positions; populating each of the plurality of placeholders with scan operation status information received from a scanning device; sequentially populating each of the placeholders with scanned images of biological samples received from the scanning device; and transmitting signals to the scanning device to effectuate rescanning of one or more slide positions based on one or more selected user configurable scanning settings.

In some embodiments is a scanning system comprising: a scanning device and a processing subsystem communicatively coupled to the scanning device, the processing subsystem configured to: display a representation of a slide tray inserted into the scanning device, the slide tray having a plurality of slide positions, wherein each slide position corresponds to one of a plurality of placeholders within the displayed representation; receive image data and scan operation status information corresponding to each of the slide positions from the scanning device; populate each of the placeholders with the received scan operation status information; sequentially populate each of the placeholders with the received image data; and send signals to the scanning device to effectuate rescanning of one or more slide positions based on selected user configurable scanning settings.

In some embodiments, the method further comprises displaying the rescanned image data pertaining to the one or more slide positions. In some embodiments, the processing subsystem is communicatively coupled to a storage subsystem for saving acquired image data and/or metadata, such as in the DICOM format. In some embodiments, the displayed representation further includes selectable elements pertaining to one or more scanning settings.

In some embodiments, rescanning for any of the slide positions occurs after a determination that an initially applied set of scanning settings did not provide image data meeting predetermined criteria. In some embodiments, the determination is facilitated by displaying at least one magnified portion of the image data and/or by displaying the scanning settings used in the acquisition of the image data.

In some embodiments, the processing subsystem displays the representation following receipt of a slide tray insertion signal from the slide scanning device. In some embodiments, the acquisition of image data and the transmission of scan operation status information is performed automatically, i.e. the processing subsystem sends a signal to the scanning device to start image acquisition and to transmit the status information after receipt of the slide tray insertion signal. In some embodiments, the automatic acquisition of image data is based on preset scanning settings. In some embodiments, image data acquisition and status information transmittal are manually initiated, i.e. the processing subsystem sends a signal to the scanning device to start image acquisition and to transmit the status information after the receipt of signals from an input device communicatively coupled to the processing subsystem. In some embodiments, the receipt of signals for the manual initiation of scanning correspond to the selection of a displayed user interface element.

In some embodiments, the displayed representation of the slide tray is a portion of a user interface, the user interface further including a plurality of user selectable configuration settings and other control elements. In some embodiments, the plurality of user selectable configuration settings comprises (i) adjustments to a pre-computed area of interest; and (ii) user configurable scanning parameters. In some embodiments, the adjustments to a pre-computed area of interest include the resizing of an area of interest, the repositioning of an area of interest, the repositioning of a focus point, the creating of a new area of interest, or the deleting of an area of interest. In some embodiments, the user configurable scanning parameters include a focus method, an AOI detection method, a magnification, a number of focus layers, and a spacing of focus layers. In some embodiments, the user configurable scanning parameters further include a label anonymization feature.

In some embodiments, the scanning operation status information includes at least one of alphanumeric indications, animations, and colored indicia. In some embodiments, the slide scanning device includes an exterior panel having a plurality of status indicator lights, each status indicator light corresponding to one of the plurality of placeholders in the user interface representation, and wherein the colored indicia displayed for any individual placeholder of the plurality of placeholders substantially matches a color of the corresponding individual status indicator light.

In some embodiments, the processing subsystem includes instructions to automatically recognizing slide label information for any slide at any slide position and populating the slide label information into one or more metadata fields. In some embodiments, the slide label information is embodied within a barcode. In some embodiments, the one or more metadata fields are DICOM attributes. In some embodiments, at least one user configurable scanning setting is automatically changed based on the automatically recognized slide label information.

In some embodiments is a non-transitory computer-readable medium storing instructions for generating high-resolution image scans of a biological sample with a slide scanning device, comprising: displaying a plurality of non-overlapping placeholders, each placeholder corresponding to a slide position of a slide tray inserted in the slide scanning device, wherein each placeholder has a first portion adapted to convey image data, and a second portion adapted to convey one or more data fields; populating the second portion of each of the plurality of placeholders with at least scanning operation status information; populating the first portion of at least one of the plurality of placeholders with a preview scan image of the biological sample located at the corresponding slide position of the slide tray; and generating at least one revised scanned image (e.g. a higher resolution image as compared with the preview scan image) based on received input signals corresponding to one or more selected user configurable scanning settings. In some embodiments, the generating of the at least one revised scanned image is made after a determination that the preview scan image of the biological sample did not meet pre-determined criteria, e.g. the image was not focused properly, an improper number of focus layers was selected, the magnification was too high to too low, etc.

In some embodiments, the non-transitory computer-readable medium also includes instructions for automatically recognizing information encoded with a barcode or otherwise provided on a label portion of a slide. In some embodiments, the non-transitory computer-readable medium also includes instructions for automatically populating one or more metadata fields with the automatically recognized information. In some embodiments, the one or more metadata fields are DICOM image attributes (e.g. patient name, case number, etc.). In some embodiments, the scanning operation status information includes at least one of alphanumeric indications, animations, and colored indicia. In some embodiments, the slide scanner device includes an exterior panel having a plurality of status indicator lights, each status indicator light corresponding to one of the plurality of placeholders, and wherein the colored indicia displayed for any individual placeholder of the plurality of placeholders substantially matches a color of the corresponding individual status indicator light. In some embodiments, an adjacent pair of slide status indicator lights correspond to a single placeholder.

In some embodiments is a graphical user interface for facilitating the acquisition of high-resolution scans of biological samples using a slide scanning device, the graphical user interface comprising a display on a computer system executed by at least one processor, wherein the graphical user interface is configured to: (i) present, on the display of the computer system, a visualization of a plurality of slide positions of a slide tray inserted into the scanning device; (ii) present, on the display of the computer system, image data and scanning status operation information received from the scanning device, wherein the display of the computer system is updated with the image data and scanning status operation information as the image data and scanning status operation information is received form the scanning device; (iii) present, on the display of the computer system, one or more interface components configured to receive one or more user inputs identifying user configurable scanning settings; (iv) accept, on the display of the computer system, the one or more user inputs identifying the user configurable scanning settings; and (v) present, on the display of the computer system, a visualization of the plurality of slide positions with rescanned image data based on the accepted user inputs identifying the user configurable scanning settings. In some embodiments, the image data received from the scanning device is presented sequentially as an image scan is completed. In some embodiments, the presented scanning operation status information is synchronized with a series of indicator lights on the exterior of the scanning device. In some embodiments, the synchronization includes substantially matching a color of the presented scanning operation status information with a color of a corresponding indicator light. In some embodiments, the received one or more user inputs identify user configurable scanning settings includes user inputs to initiate scanning of a high-resolution image without changes to user configurable scanning settings.

In some embodiments, the user selectable configuration settings comprise (i) adjustments to a pre-computed area of interest; and (ii) user configurable scanning parameters. In some embodiments, the adjustments to a pre-computed area of interest include the resizing of an area of interest, the repositioning of an area of interest, the repositioning of a focus point, the creating of a new area of interest, or the deleting of an area of interest. In some embodiments, the user configurable scanning parameters include a focus method, an AOI detection method, a magnification, a number of focus layers, and a spacing of focus layers. In some embodiments, the user configurable scanning parameters further include a label anonymization feature.

In some embodiments is a method of acquiring a high-resolution image of a biological sample with a slide scanning device, comprising: displaying a user interface, the user interface having a plurality of placeholders, each placeholder corresponding to a slide position of a slide tray inserted into the slide scanning device, wherein each placeholder has a first portion adapted to convey an image of a biological sample disposed on a slide at the corresponding slide position of the slide tray, and a second portion adapted to at least convey scanning operation status indications; populating the second portion of each of the plurality of placeholders with the scanning operation status indications; populating at least one of the plurality of placeholders with an initial thumbnail image of the biological sample located at the corresponding slide position of the slide tray; displaying a plurality of user configurable scanning parameters, the user configurable scanning parameters being independently applicable to any initial scanned thumbnail image populated in the plurality of placeholders; generating the high-resolution image corresponding to the initial scanned thumbnail image in any of the populated plurality of placeholders based on received input signals corresponding to one or more selected user configurable scanning parameters; and storing the generated high-resolution image. In some embodiments, the plurality of placeholders are non-overlapping and equally sized. In some embodiments, the user interface also includes menu bars and configuration panels.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method of acquiring high-resolution images of a biological sample with a slide scanning device, the method comprising:
    displaying a plurality of non-overlapping placeholders, each placeholder corresponding to a slide position of a slide tray inserted in the slide scanning device, wherein each placeholder has a first portion adapted to convey image data, and a second portion adapted to convey one or more data fields;
    populating the second portion of each of the plurality of non-overlapping placeholders with at least scanning operation status information that identifies a status of a scanning operation performed by the slide scanning device;
    populating the first portion of at least one of the plurality of non-overlapping placeholders with a preview scan image of the biological sample located at a corresponding slide position of the slide tray;
    receiving, for a preview scan image of a placeholder of the plurality of non-overlapping placeholders, input signals corresponding to an adjustment of a pre-computed area of interest used by the slide scanning device, wherein the adjustment includes resizing of the pre-computed area of interest or deletion of the pre-computed area of interest; and
    rescanning, based on the resizing or deletion of the pre-computed area of interest indicated by the received input signals, the biological sample of the preview scan image to generate at least one high resolution scanned image corresponding to the preview scan image.

2. The method of claim 1, wherein the preview scan image is a thumbnail image.

3. The method of claim 1, wherein the adjustment to the pre-computed area of interest further includes at least one of repositioning of the pre-computed area of interest, repositioning of a focus point of the pre-computed area of interest, or creation of a new area of interest.

4. The method of claim 1, wherein the input signals further include additional adjustments to at least one of an AOI detection method, a magnification, a number of focus layers, or a spacing of focus layers.

5. The method of claim 4, wherein the additional adjustments further include label anonymization.

6. The method of claim 1, wherein both scanning operation status information and initial scanning parameters are displayed in the second portion of the plurality of non-overlapping placeholders.

7. The method of claim 1, wherein the scanning operation status information populated in the second portion of the placeholder is an empty status field when no slide is present in the corresponding slide position in the slide tray.

8. The method of claim 1, wherein the preview scan image populated into the first portion of the at least one of the plurality of non-overlapping placeholders is automatically generated, and wherein the preview scan image is acquired using pre-programmed scanning settings.

9. The method of claim 8, wherein the pre-programmed scanning settings include at least one of a focus method and an area of interest detection method.

10. The method of claim 1, wherein the scanning operation status information includes at least one of alphanumeric indications, animations, and colored indicia.

11. The method of claim 10, wherein the slide scanning device includes an exterior panel having a plurality of status indicator lights, each status indicator light corresponding to one of the plurality of non-overlapping placeholders, and wherein the colored indicia displayed for any individual placeholder of the plurality of non-overlapping placeholders substantially matches a color of a corresponding individual status indicator light.

12. The method of claim 1, further comprising automatically recognizing slide label information and populating the recognized slide label information into one or more metadata fields.

13. The method of claim 12, wherein the one or more metadata fields are DICOM attributes.

14. The method of claim 1, further comprising evaluating whether the preview scan image within the at least one of the plurality of non-overlapping placeholders meets predetermined criteria, wherein the evaluation of the preview scan image comprises reviewing at least one magnified portion of the preview scan image for focus quality or image contrast.

15. The method of claim 1, further comprising displaying a superimposed window including a rendering of a magnified portion of the preview scan image populated into the first portion of the at least one of the plurality of non-overlapping placeholders.

16. The method of claim 15, wherein the rendering of the magnified portion of the preview scan image corresponds to an image area selected with an input device.

17. The method of claim 1, further comprising superimposing the pre-computed area of interest over the preview scan image populated into the first portion of the at least one of the plurality of non-overlapping placeholders.

18. The method of claim 1, wherein each of the non-overlapping plurality of placeholders are sequentially populated with preview scan images of the biological sample at corresponding slide positions of the slide tray, and wherein the scanning operation status information is updated in real-time.

19. The method of claim 1, further comprising receiving a slide tray insertion signal, the slide tray insertion signal including an indication of a number of slide positions within the slide tray, and wherein a number of the plurality of non-overlapping placeholders to be displayed is determined based on the indicated number of slide positions.

20. A system for generating high-resolution image scans, the system comprising: (i) one or more processors, and (ii) one or more memories coupled to the one or more processors, the one or more memories to store computer-executable instructions that, when executed by the one or more processors, cause the system to perform operations comprising:
displaying a representation of a slide tray having a plurality of slide positions on a display device, wherein the representation includes a plurality of placeholders, each placeholder corresponding to one of the plurality of slide positions;
populating each of the plurality of placeholders with scanning operation status information received from a scanning device, wherein the scanning operation status information identifies a status of a scanning operation performed by a slide-scanning component of the system;
sequentially populating each of the placeholders with a corresponding preview scanned image of a biological sample received from the scanning device;
transmitting signals to the scanning device to effectuate scanning of one or more microscope slides located at one or more slide positions of the slide tray based on one or more selected user configurable scanning settings;
receiving, for a particular preview scan image of a placeholder of the plurality of placeholders, input signals corresponding to an adjustment of a pre-computed area of interest used by the slide-scanning component of the system, wherein the adjustment includes resizing of the pre-computed area of interest or deletion of the pre-computed area of interest; and
rescanning, based on the resizing or deletion of the pre-computed area of interest indicated by the received input signals, the biological sample of the particular preview scan image to generate at least one high resolution scanned image corresponding to the particular preview scan image.

21. The system of claim 20, wherein the computer-executable instructions further cause the system to perform operations comprising displaying a magnified portion of at least one of the preview scanned images.

22. The system of claim 21, wherein the magnified portion is displayed in a superimposed viewer window.

23. The system of claim 20, wherein the one or more selected user configurable scanning settings comprise configurable scanning parameters.

24. The system of claim 20, wherein the adjustment to a pre-computed area of interest further includes at least one of repositioning of the pre-computed area of interest, repositioning of a focus point of the pre-computed area of interest, or creation of a new area of interest.

25. The system of claim 23, wherein the configurable scanning parameters include a focus method, an AOI detection method, a magnification, a number of focus layers, and a spacing of focus layers.

26. The system of claim 20, wherein the scanning operation status information includes at least one of alphanumeric indications, animations, and colored indicia.

27. The system of claim 26, wherein the scanning device includes an exterior panel having a plurality of status indicator lights, each status indicator light corresponding to one of the plurality of placeholders, and wherein the colored indicia displayed for any individual placeholder of the plurality of placeholders substantially matches a color of a corresponding individual status indicator light.

28. The system of claim 20, wherein the computer-executable instructions further cause the system to perform operations comprising automatically recognizing slide label information within the preview scanned images and populating the slide label information into one or more metadata fields.

29. The system of claim 28, wherein the one or more metadata fields are DICOM attributes.

30. A non-transitory computer-readable medium storing instructions for generating high-resolution image scans with a slide scanning device, comprising:
displaying a plurality of non-overlapping placeholders, each placeholder corresponding to a slide position of a slide tray inserted in the slide scanning device, wherein each placeholder has a first portion adapted to convey image data, and a second portion adapted to convey one or more data fields;
populating the second portion of each of the plurality of non-overlapping placeholders with at least scanning operation status information that identifies a status of a scanning operation performed by the slide scanning device;
populating the first portion of at least one of the plurality of non-overlapping placeholders with a preview scan image of a biological sample located at a corresponding slide position of the slide tray;
receiving, for a preview scan image of a placeholder of the plurality of non-overlapping placeholders, input signals corresponding to an adjustment of a pre-computed area of interest used by the slide scanning device, wherein the adjustment includes resizing of the pre-computed area of interest or deletion of the pre-computed area of interest; and
rescanning, based on the resizing or deletion of the pre-computed area of interest indicated by the received input signals, the biological sample of the preview scan image to generate at least one high resolution scanned image corresponding to the preview scan image.

31. The non-transitory computer-readable medium of claim 30, wherein instructions are provided to automatically initiate a scanning operation upon insertion of the slide tray into the slide scanning device.

32. The non-transitory computer-readable medium of claim 31, wherein the automatically initiated scanning operation utilizes preset scanning settings.

33. The non-transitory computer-readable medium of claim 32, wherein the preset scanning settings include at least one of a focus method and an area of interest detection method.

34. A method of acquiring a high-resolution scan of a biological sample disposed on a substrate with a scanning device, the method comprising:
receiving, on a graphical user interface, a first user input corresponding to user configurable scanning settings;
receiving, on a graphical user interface, a second user input to initiate scanning based on the first user input corresponding to the user configurable scanning settings;
displaying, on the graphical user interface, at least a visualization of one or more placeholders populated with one or more of (i) scanning operation status information, (ii) image data, and/or (iii) at least a portion of the user configurable scanning settings, wherein the scanning operation status information identifies a status of a scanning operation performed by a slide scanning device;

receiving a third user input to rescan the image data based on a revised series of user inputs corresponding to user configurable scanning settings, wherein the revised series of user inputs include an adjustment of a pre-computed area of interest used by the slide scanning device, wherein the adjustment includes resizing of the pre-computed area of interest or deletion of the pre-computed area of interest; and rescanning, based on the resizing or deletion of the pre-computed area of interest indicated by the third user input, the image data to generate a high-resolution scan of the image data.

35. The method of claim 34, further comprising receiving a fourth user input to store the image data.

36. The method of claim 35, wherein the storing of the image data further comprises generating the high-resolution scan of the image data prior to storage.

37. The method of claim 34, wherein the adjustment to the pre-computed area of interest further includes at least one of repositioning of the pre-computed area of interest, repositioning of a focus point of the pre-computed area of interest, or creation of a new area of interest.

38. The method of claim 34, wherein the revised series of user inputs further include additional adjustments to at least one of an AOI detection method, a magnification, a number of focus layers, or a spacing of focus layers.

39. The method of claim 38, wherein the additional adjustments further include label anonymization.

40. The method of claim 34, wherein the scanning operation status information includes at least one of alphanumeric indications, animations, and colored indicia.

* * * * *